United States Patent [19]
Hutchinson et al.

[11] Patent Number: 6,152,563
[45] Date of Patent: Nov. 28, 2000

[54] EYE GAZE DIRECTION TRACKER

[76] Inventors: Thomas E. Hutchinson, P.O. Box 168, Ivy, Va. 22945; Christopher Lankford, 109 Clarke Ct. Apt. 203, Charlottesville, Va. 22903; Peter Shannon, 3419 Greentree Dr., Falls Church, Va. 22041

[21] Appl. No.: 09/027,511

[22] Filed: Feb. 20, 1998

[51] Int. Cl.$^7$ .......................................................... A61B 3/14
[52] U.S. Cl. .............................................................. 351/209
[58] Field of Search ................................... 351/205, 209, 351/210, 211, 221, 246

[56] References Cited

U.S. PATENT DOCUMENTS 5,861,940  1/1999  Robinson et al. ...................... 351/221

*Primary Examiner*—George Manuel
*Attorney, Agent, or Firm*—James W. Hiney

[57] ABSTRACT

A system for eye-gaze direction detection is disclosed that uses an infrared light emitting diode mounted coaxially with the optical axis and in front of the imaging lens of an infrared sensitive video camera for remotely recording images of the eye of the computer operator. The infrared light enters the eye and is absorbed and then re-emitted by the retina, thereby causing a "bright eye effect" that makes the pupil brighter than the rest of the eye. It also gives rise to an even brighter small glint that is formed on the surface of the cornea. The computer includes software and hardware that acquires a video image, digitizes it into a matrix of pixels, and then analyzes the matrix to identify the location of the pupil's center relative to the glint's center. Using this information, the software calibrates the system to provide a high degree of accuracy in determining the user's point of regard. When coupled with a computer screen and a graphical user interface, the system may place the cursor at the user's point of regard and then perform the various mouse clicking actions at the location on the screen where the user fixates. This grants the individual complete control over the computer with solely their eye. The technology is not limited to determining gaze position on a computer display; the system may determine point of regard on any surface, such as the light box radiologists use to study x-rays.

12 Claims, 14 Drawing Sheets

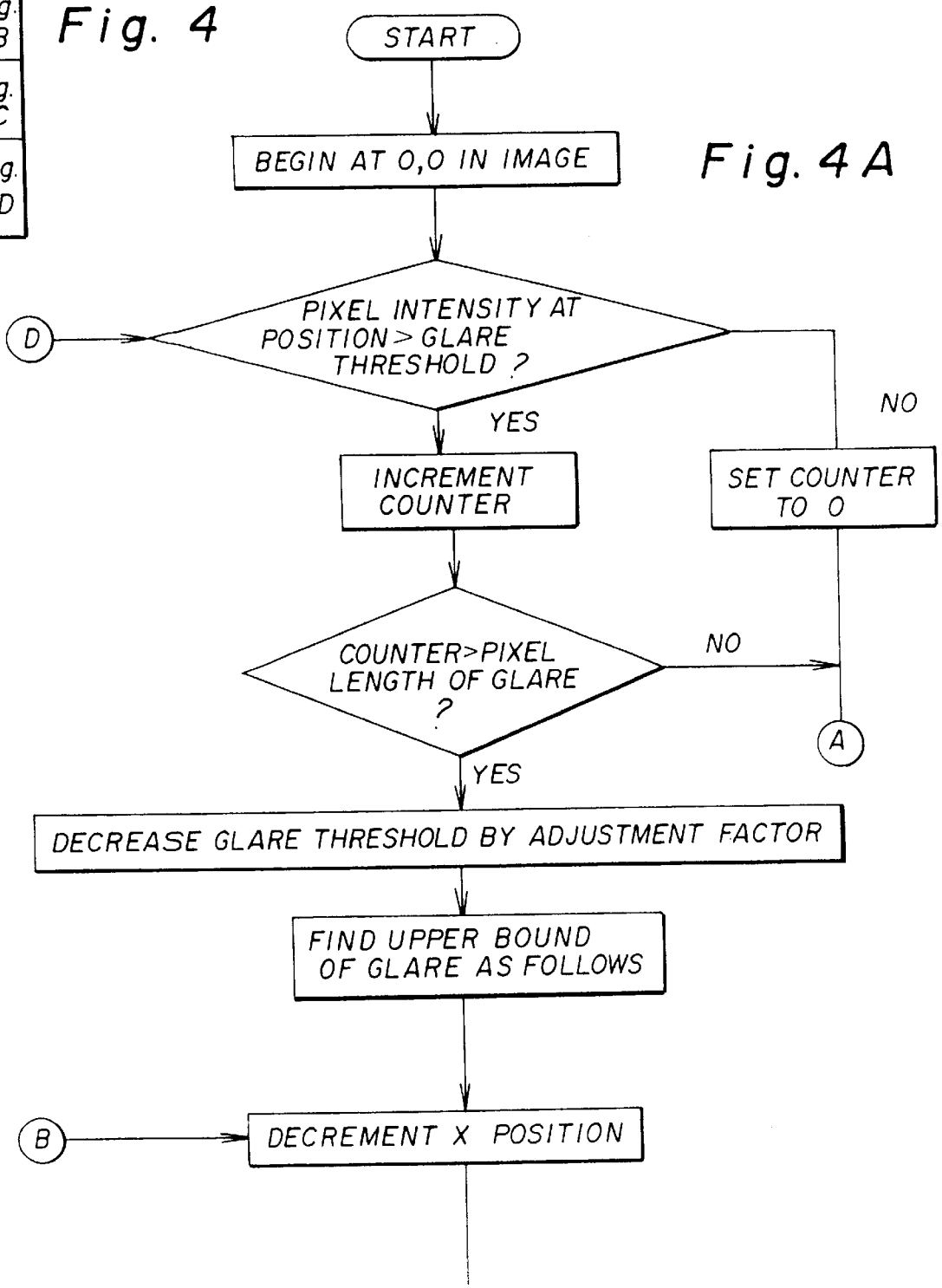

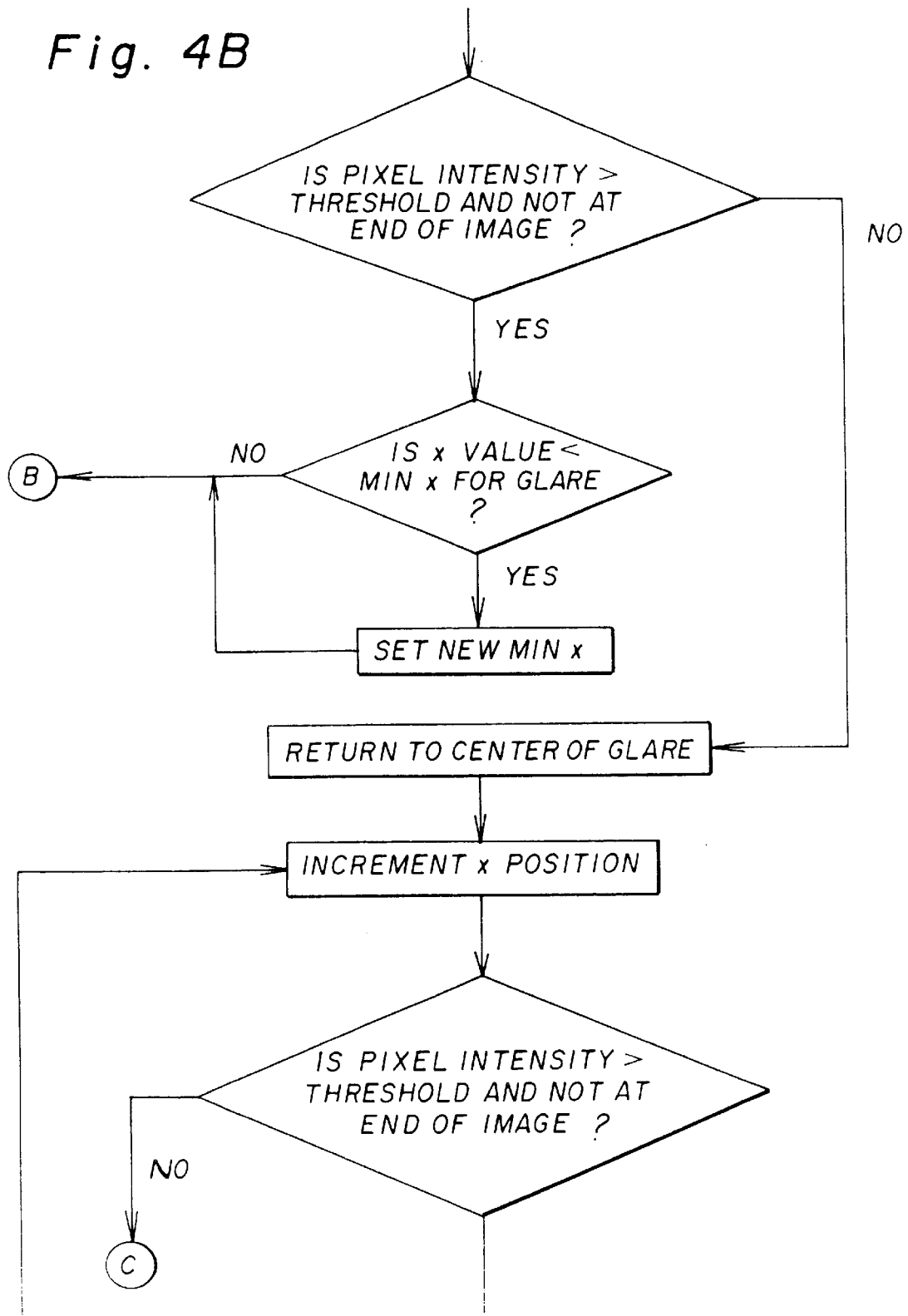

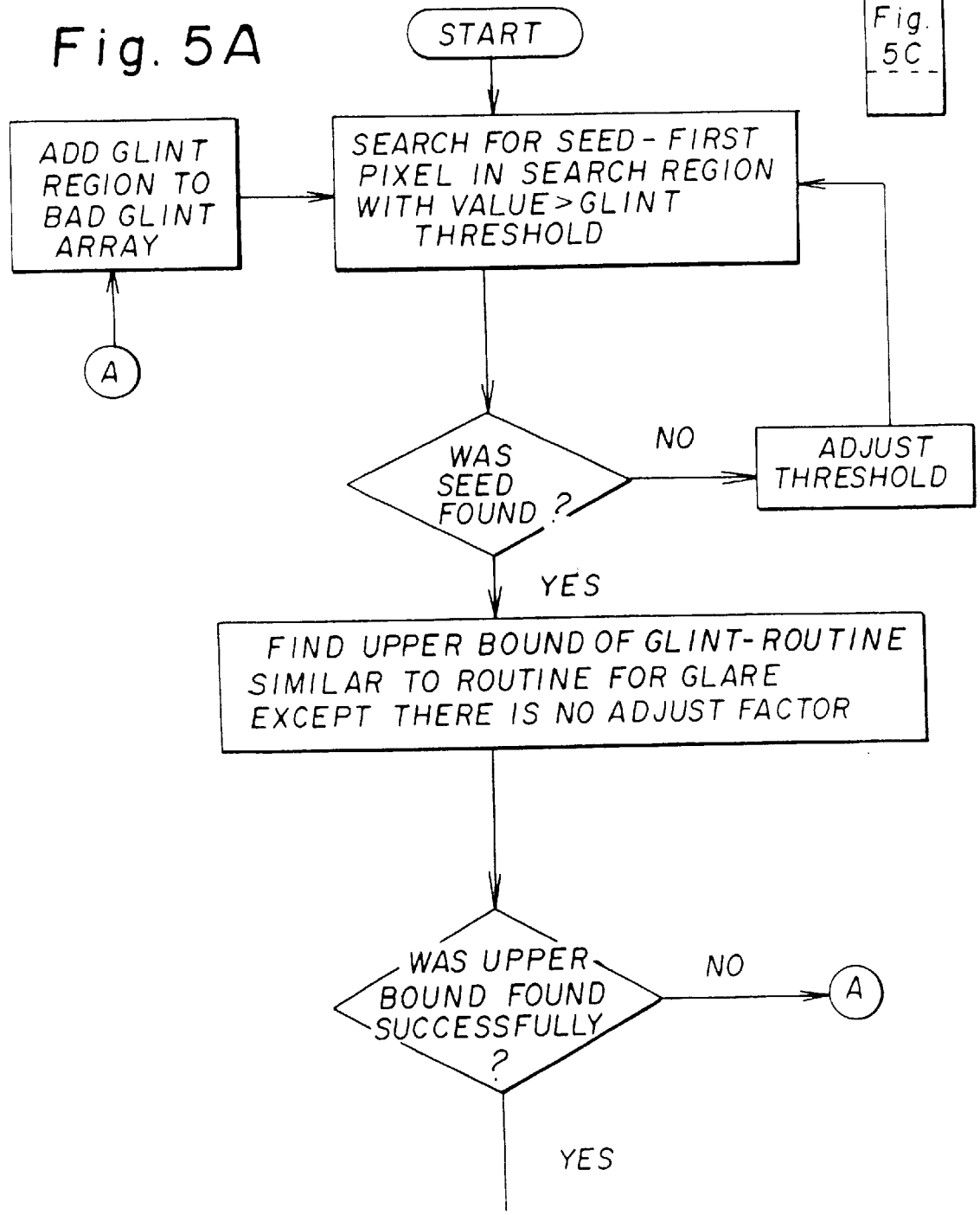

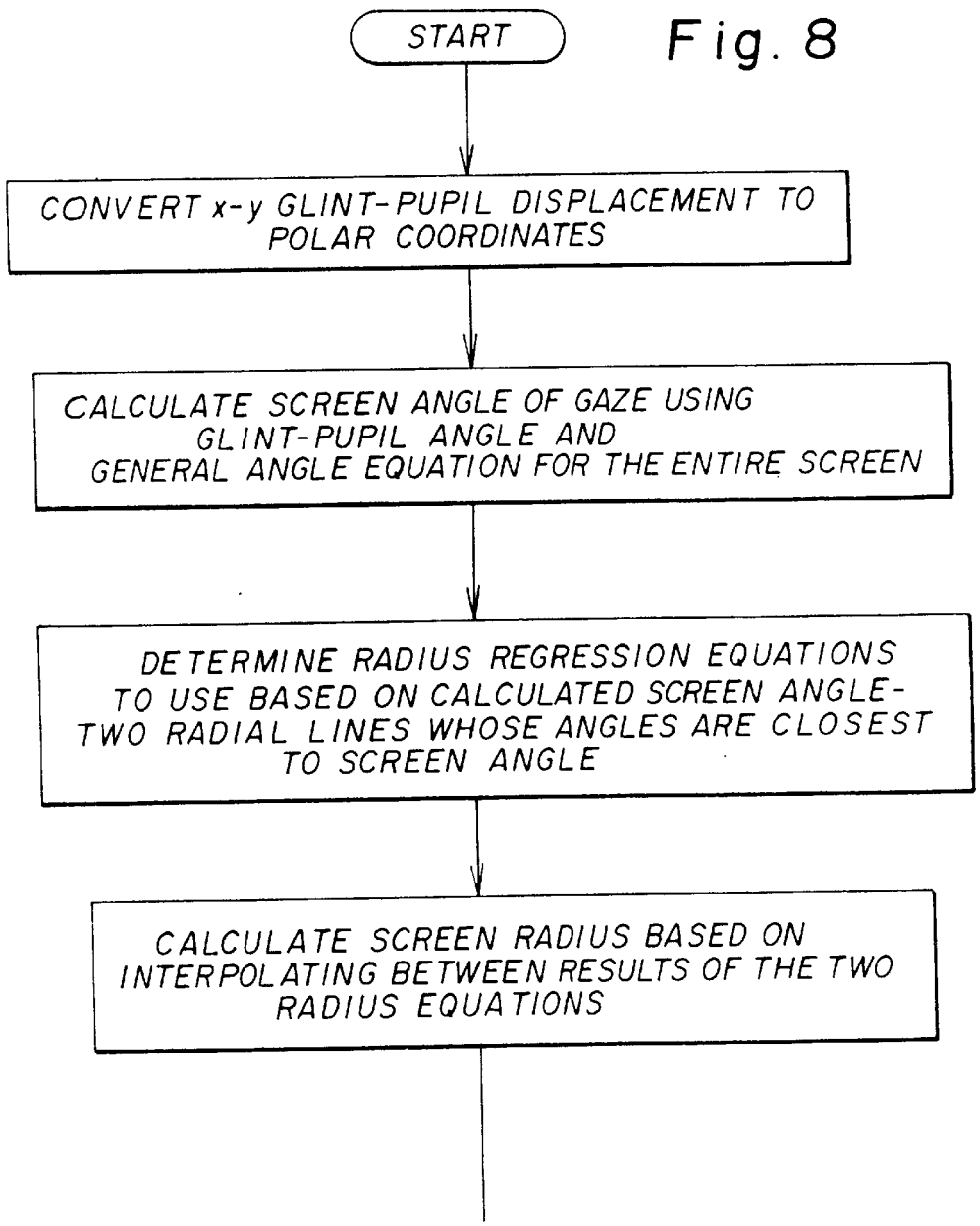

EYE GAZE DIRECTION TRACKER

This invention describes an eye-gaze direction detecting device which is utilized as a means of interfacing a person with a computer.

The present invention is an improvement over the invention disclosed in U.S. patent application Ser. No. 267,266 filed on Nov. 4, 1988 now U.S. Pat. No. 4,950,069 which disclosure is hereby incorporated herein and made a part hereof. The improvement relates to a new calibration arrangement granting greater accuracy, better algorithms that allow a more robust determination of pupil-glint displacement, and features that allow an operator to effectively exploit a graphical user interface (GUI).

There are a number of eye-gaze direction detector techniques. Some of these have been applied to assist a handicapped person such as a quadriplegic who has lost many of his or her physical abilities and may have even lost the ability to speak clearly. Many of these severely handicapped people still have control over their direction of gaze and all of their mental faculties. Thus, a device that enables them to fully operate a computer with their eye and therefore communicate messages and maintain productivity is a great benefit both physically and psychologically. As used in this disclosure, "eye-gaze direction detector" refers generically to any technology related to detecting either movement of the eye or eye-gaze direction.

One of the eye movement technologies is electrooculography, which uses the difference in voltage between the cornea and the retina of the eye. Another technology is corneal reflection which uses the reflection of a beam of light from the various surfaces of the eye the beam crosses. The brightest reflection is the outer corneal surface (first Purkinje image) with the second, third, and fourth Purkinje images being dimmer and corresponding respectively to the inner surface of the cornea and the outer and inner surfaces of the lens. Usually the reflections from the outer surface of the cornea and the inner surface of the lens are the two utilized.

A third technology is limbus tracking that detects the generally sharp boundary between the iris and the sclera (the white part of the eye). A fourth technology is the use of a contact lens that rotates with the eye and is fitted with various devices to determine the amount of eye rotation. A fifth technique is to measure the eccentricity of the pupil which varies from circular when viewed head on to elliptical as it rotates away from the axis in which it is viewed. A sixth technique is a movement measurement based on the head and eyes being moved together. A seventh technique is the oculometer that determines the center of the pupil and the corneal highlight from a reflected light and the change in the distance and direction between the two as the eye is rotated. Additional techniques exist, but these are the major ones. Some of them incorporate a head or eye mounted devices whereas others permit the eye-gaze direction detector to be mounted remote to the head.

The present invention relates specifically to the category of oculometer eye measurement detectors but some aspects of the invention can also be utilized with other techniques. The invention is primarily designed to provide an eye-driven method of interfacing a person with the computer. This is of fundamental interest to handicapped individuals who would benefit greatly from an eye-driven device. When a healthy functional person suddenly loses their ability to act for themselves and to communicate, the mind becomes trapped within the body. The need to communicate and remain productive becomes more acute for the individual when they are robbed of motor functions and speech.

Complete motor dysfunction occurs as a result of both traumatic spinal injuries and gradual paralysis during the course of peripheral neuromuscular diseases. It affects young children by making them grow up in mental and physical isolation without a way to educate their minds or to acquire skills for an adult life. It also affects adults who are accustomed to a normal lifestyle and who must learn to cope with the resulting severe form of isolation from family, friends, and others who must now care for them.

Use of the present invention prevents this isolation by allowing the individual to have complete control over a computer with their eye. This grants the person the ability to effectively communicate on his or her own. Also, in a society where computers are becoming increasing pervasive, this allows a handicapped person to remain productive and possibly employed. This greatly increases the quality of the handicapped person's life and the lives of those who care for them.

While the invention has been primarily developed for handicapped persons, the technology may also be used for industrial control, cockpit control, video game control, workstation control, and other applications where eye-gaze control is desired. The invention may also be used for testing and training purposes based on eye movement, such as testing or training radiologists to read x-rays.

Because of the physiological make-up of the human eye, the eye normally directs its gaze with a very high degree of accuracy at the gaze point. This is due to the photoreceptors of the human retina not being uniformly distributed but instead show a pronounced density peak in a small region known as the fovea. In this region, which subtends a visual angle for about 1°, the receptor density increases to about 10 times the average density. The nervous system controls the muscles attached to the eye to keep the image of the region of current interest centered accurately on the fovea as this gives the high resolution. The appearance of high resolution at all directions outside of this region is thus an illusion maintained by a combination of physiological mechanisms (rapid scanning with brief fixations), and psychological ones. As an example, a character on a typical computer display screen subtends an angle of about 0.3° at a normal viewing distance. Such characters cannot be accurately resolved unless the eye is accurately aligned for a duration of 0.2 seconds.

The eye-gaze direction detecting system described here is designed to allow control over the computer through dwell time activation of commands normally controlled by mouse clicks. By fixating on an area of the computer display, the system performs a user selected mouse action at that position, thus granting the user the same control over the computer that is allowed by a conventional mouse.

The main components of the system include a charge-coupled device (CCD) camera sensitive to the near infrared with a 300 mm zoom lens and a coaxially mounted infrared light source. An infrared filter allows primarily infrared light to reach the camera. This assembly is housed inside a module that rests beneath the computer monitor. The module employs a folded optical arrangement that directs the camera's line of sight to the user's eye through the use of two mirrors. This keeps the system relatively small and unobtrusive. One of the primary advantages of the system is that it does not require any devices to be fixed to body of the user. The camera is coupled to an inexpensive computer that contains a frame grabber or image processing board. The board digitizes video images of the eye acquired by the video camera, and the algorithms forming a part of this invention then process the image.

The operant image consists of a video image encompassing one side of the user's face. It contains the iris and sclera (both dark), the reemission of the infrared light out of the pupil (bright eye), and the corneal reflection of the infrared light source (glint). An in-focus bright eye image gives a high contrast boundary at the pupil perimeter making it easily distinguishable. The system computes the relative x-y coordinates between the glint center and the pupil center as determined by the pattern recognition software incorporated in this patent. One of the improvements to the pattern recognition software is the inclusion of algorithms that enable individuals with glasses to use the system. Glasses create extraneous reflections from the rims and lenses (glares). These reflections can possibly make pupil and glint identification difficult. The new improvements essentially remove a majority of these added reflections from the image thereby allowing individuals with glasses to benefit from an eye-controlled device.

The glint and the bright eye are features produced by the infrared light emitted by the semiconductor diode, mounted coaxial with the video camera lens. The illumination is invisible to the user and has a principle advantage of producing very little subject awareness of the monitoring process. Since the light source is in coaxial alignment with the video camera lens, it results in light re-emitted back from the retina which effectively backlights the pupil so that it appears as a bright disk. This is the bright eye effect and provides a distinctive contrast to the rest of the eye or facial details. This greatly facilitates the determination of the periphery of the pupil so that the center of the pupil can be accurately calculated, which is an important feature in an oculometer. The system measures the differential between the pupil center and glint center and uses this data to compute where the eye is gazing.

The system detects when the eye lingers for a predetermined period at any position on the display. If the predetermined linger period is exceeded, then the system magnifies the area the user was looking at. A window at or near the center of the screen appears and the magnified area is placed in this window. The user then fixates in the magnified area at a point where they wish for a mouse action to be performed. After the predetermined fixation period has expired, a menu appears that allows the user to select what mouse action they wish to perform—left mouse button drag, left mouse button single click, left mouse button double click, right mouse button drag, right mouse button single click, or right mouse button double click. After fixating on the menu command for a predetermined amount of time, the system then performs the desired mouse action at the position fixated on in the magnified area.

Thus, the present invention determines eye gaze position using effects generated by infrared light. An infrared light emitting diode mounted at the center of the video camera lens illuminates the user's face with infrared light. A small fraction of the light entering the eye is absorbed and re-emitted by the retina, creating an image that is the same phenomenon which causes the pink eye effect in photography where the flash bulb is located close to the optical axis of the camera. Basically, it causes the pupil to be brighter than the rest of the eye whereas it is usually darker than the remainder of the eye. The cornea reflects an intense virtual image of the light emitting source and is referred to as the glint. The glint is usually located within the pupil's image or along or near its outer circumference.

The computer contains a frame grabber card that is commercially available and captures a frame of the video camera as a 640×480×8 bit frame. The pattern recognition software of the present invention calculates eye-gaze direction by determining the distance and angle between the glint center and pupil center. To do this, the system first obtains the intensity thresholds between the glint and the surrounding portions of the eye and then between the pupil and the surrounding portions of the eye. This step is called threshold setting. Upon completing threshold setting, the system may then accurately calculate the displacement measurements between the glint and pupil center. To effectively control the computer, the user must undergo the next step, calibration. Completion of this step, which entails the user looking at a sequence of fixed points on the screen, allows the software to map a particular glint-pupil displacement to a particular point on the screen. Thus, the user may operate the computer using solely their eye.

The following figures illustrate the setup of the system and serve to facilitate an understanding of how the system operates as described below.

FIG. 1 shows the equipment used and the optical path of the system.

FIG. 2 describes how the glint-pupil relationships change as the user looks at different positions on the screen.

FIG. 3 is a flowchart for the basic procedure used in the threshold determination algorithm.

FIG. 4 describes the glare removal algorithm.

Figure 8B:
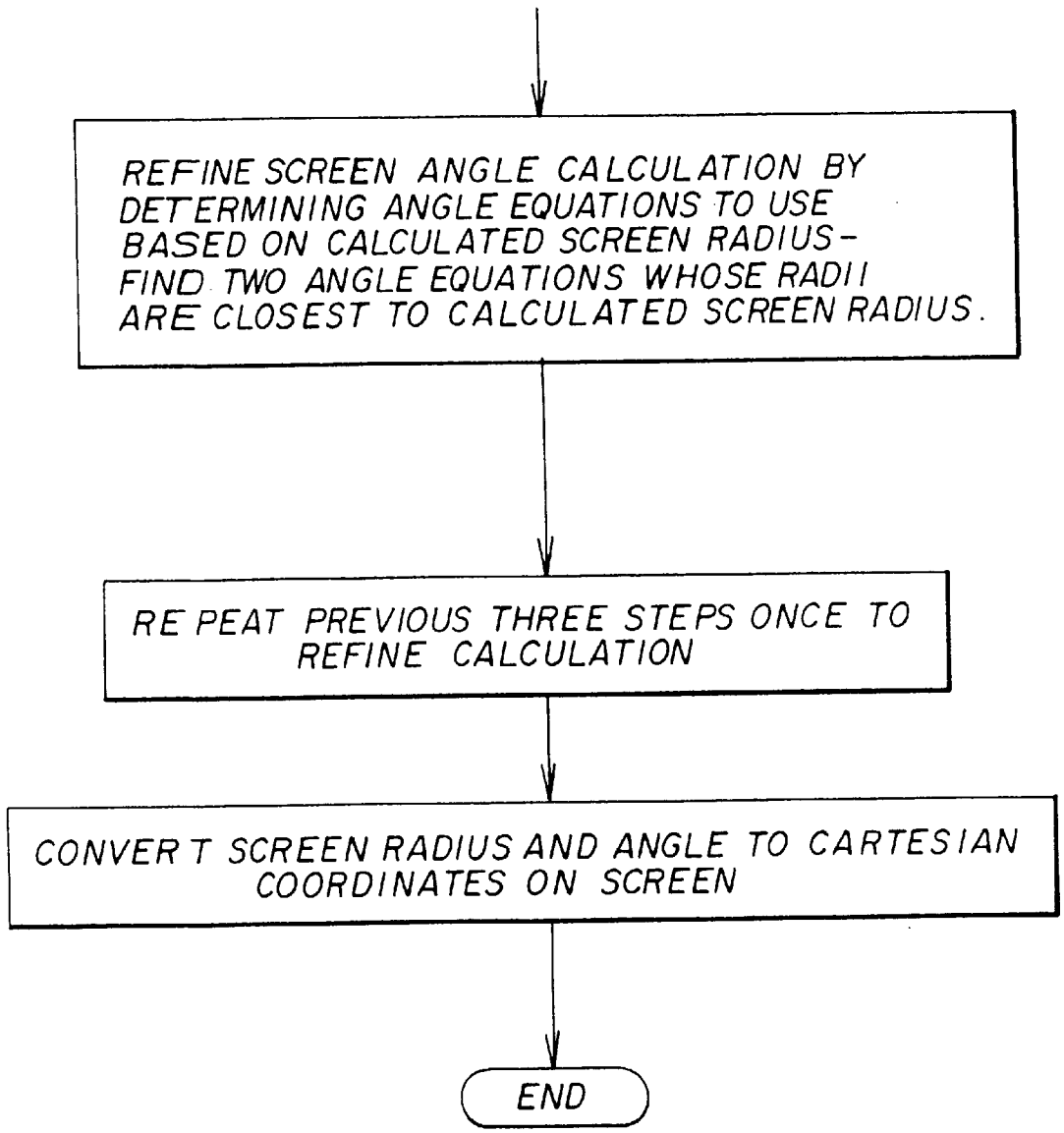

FIG. 8 describes how the system maps the glint-pupil displacement to a particular position on the screen.

Figure 9:
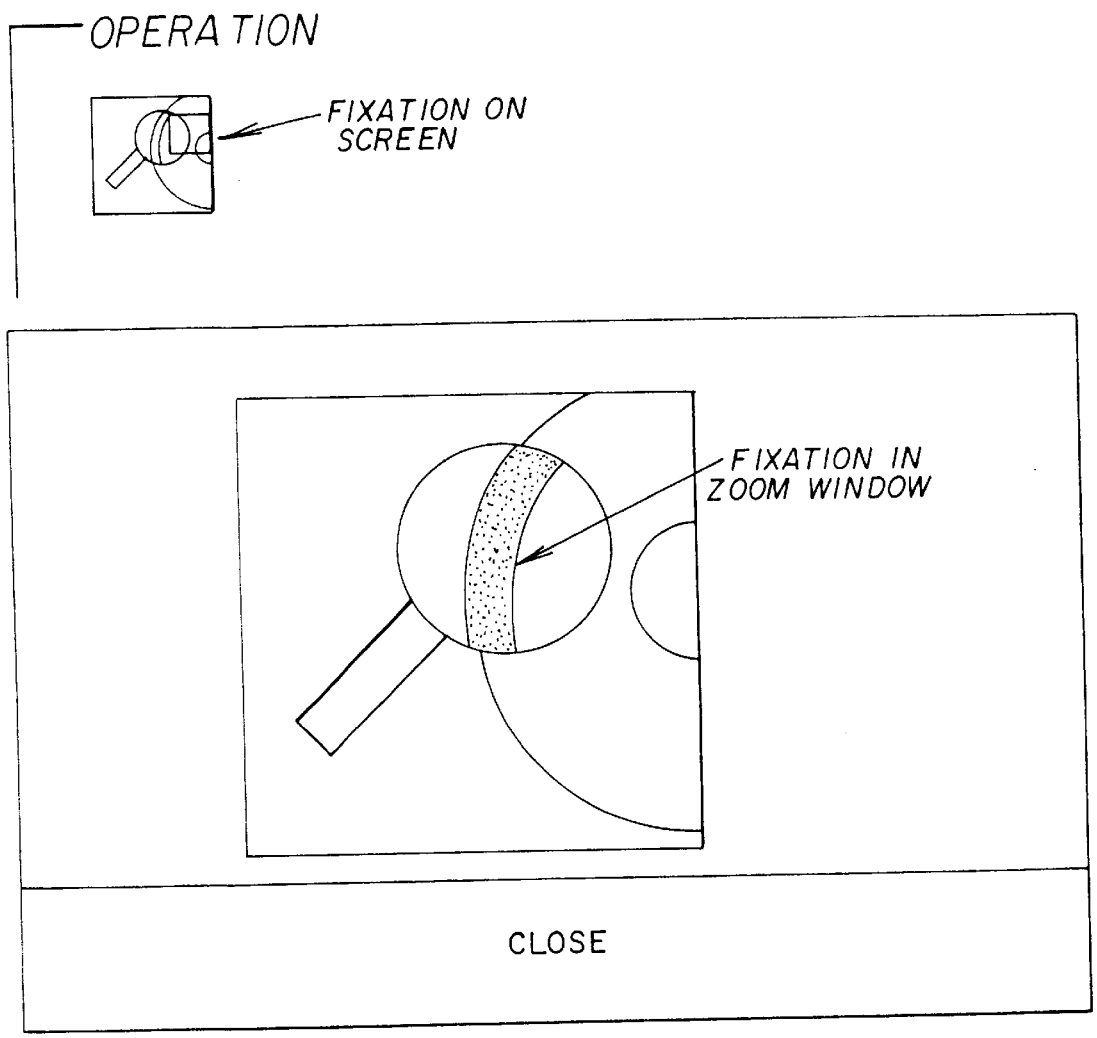

FIG. 9 shows how the zooming feature with the system works.

Figure 10:
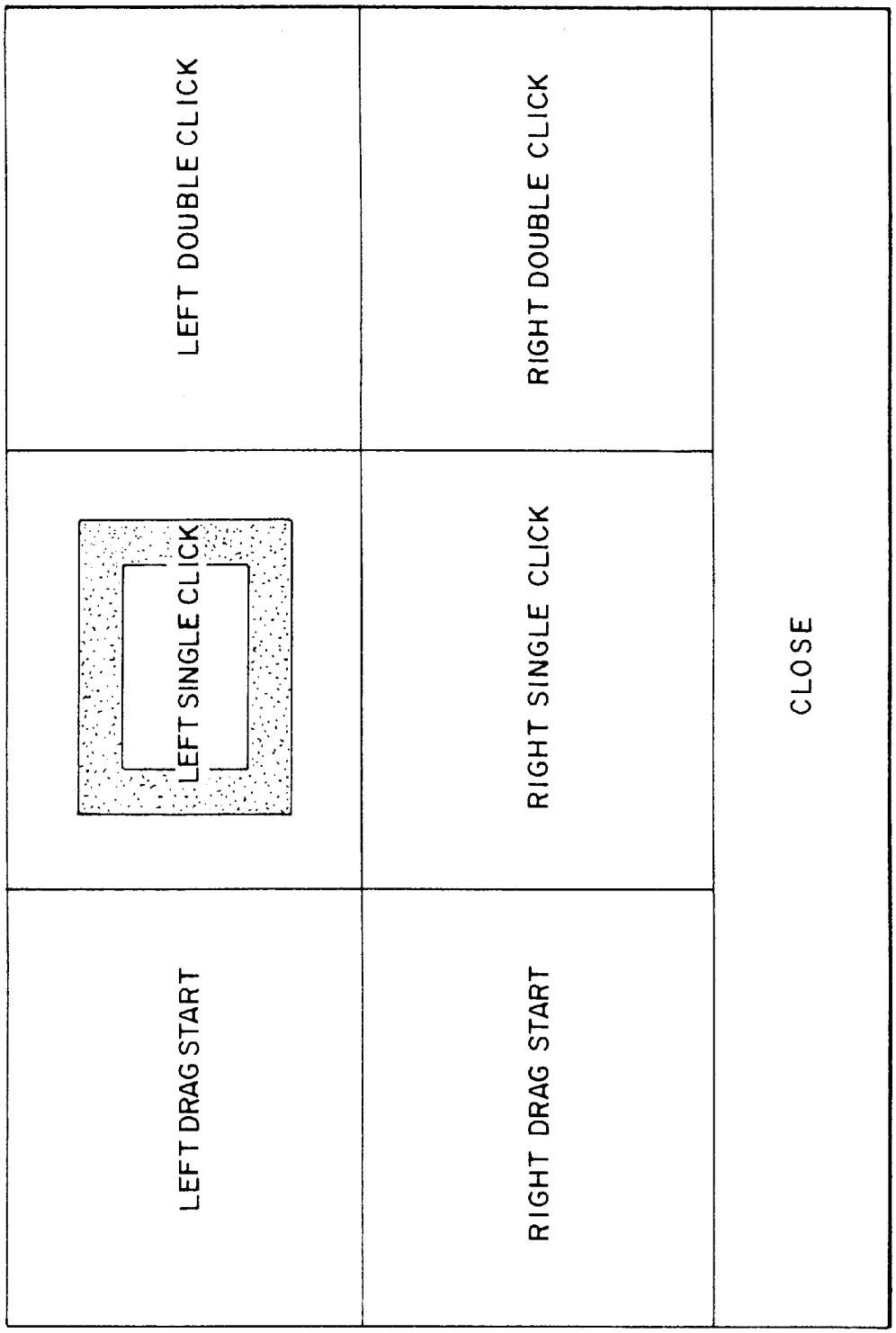

FIG. 10 shows the menu for activating mouse control actions.

Figure 1:
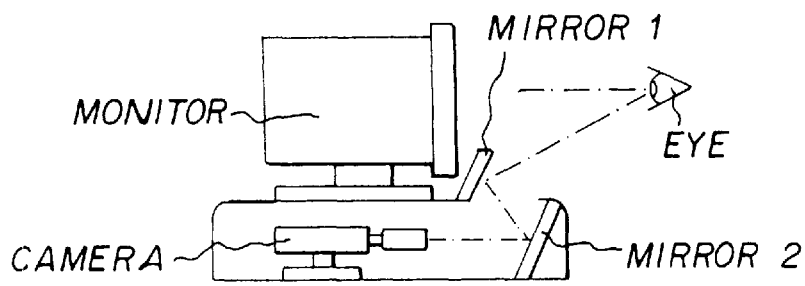

FIG. 1 shows the setup of the system. The setup includes a standard computer display resting on top of a module that houses the eye-tracking equipment. Two mirrors on the module direct the camera's line of sight to the user's eye. The computer display sits so that the image of the camera in the mirror is at the center horizontally of the computer display.

The current camera employed is the Hitachi KP-160 camera but other cameras can perform the same job. The lens is a 300 mm zoom lens but again most any lens with suitable magnification would allow the device to operate.

The infrared light emitting source is a readily available gallium arsenide diode. They are approximately 1 to 3 cm in diameter and are normally used for communication purposes with a narrow light beam dispersion as opposed to some types that send light in all directions and are used mainly as indicator lights. They usually have a small built in molded clear lens that condenses the light into a narrow beam. Additionally, the diode is placed in a plastic tube that serves to condense the beam further and to ensure that the infrared light striking the eye does so by following the optical path shown in figure one and not by bypassing the mirrors altogether. This would give a double glint in the camera image and decrease the reliability in determining the proper glint-pupil displacement. The diode preferred emits a focussed beam of light at a wavelength of 880 nm, but wavelengths as high as 900 nm are acceptable. This wavelength is invisible to the user and of a sufficiently low intensity such that it is safe for continuous use by the operator. The diode is mounted at the center of a filter screwed onto the lens. This filter blocks most visible light, allowing the infrared to pass through with little decrease in intensity.

The secondary monitor normally placed by the side of the computer monitor shows the eye image seen by the camera and allows the user to ensure that they are in focus and properly positioned in front of the video camera.

Figure 2:
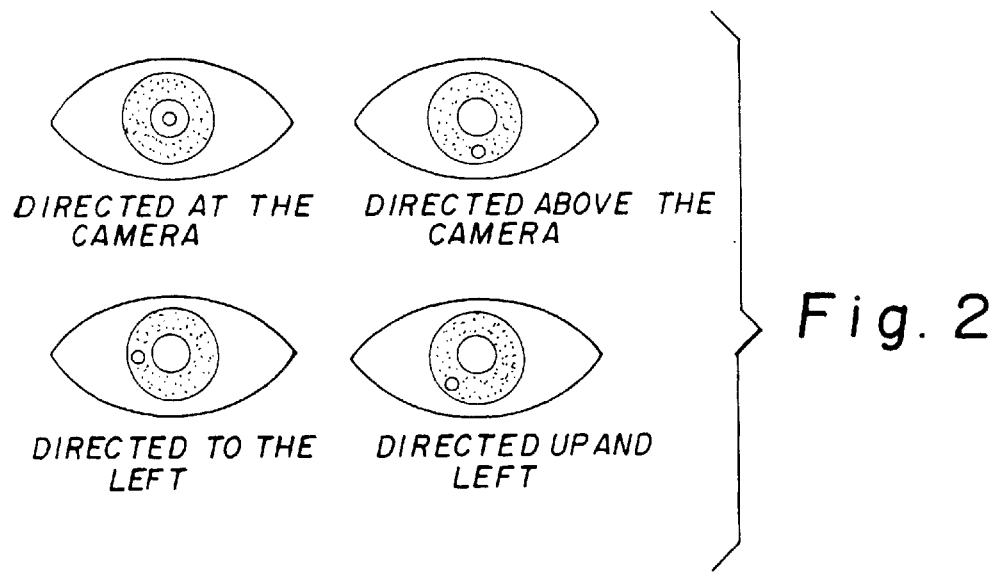

FIG. 2 describes qualitatively the glint-pupil relationships seen as the user gazes at different positions on the display. When the user looks directly back into the camera, the glint is approximately at the pupil's center. As they look directly above the camera, the glint center drops below the pupil center. When the user looks to the left, the glint center moves to the left, so the glint is to the bottom left of the pupil center. As the user looks to the right, the glint center moves to the right of the pupil center.

Installed inside the computer is a Matrox Meteor frame grabber card that acquires images from the video camera, but any compatible frame grabber card will do. The card uses the RS-170 standard to acquire an image, digitizes it into a sequence of pixels, and maps those pixel values into system memory. This results in a 640×480 resolution image with each pixel having a value from 0 to 255, with 0 being black and 255 being white. The intensity values in between represent different shades of gray.

ERICA HQ is the software program that provides an interface for manipulating the setup of the eye-controlled mouse and for undergoing calibration and threshold setting.

Figure 3:
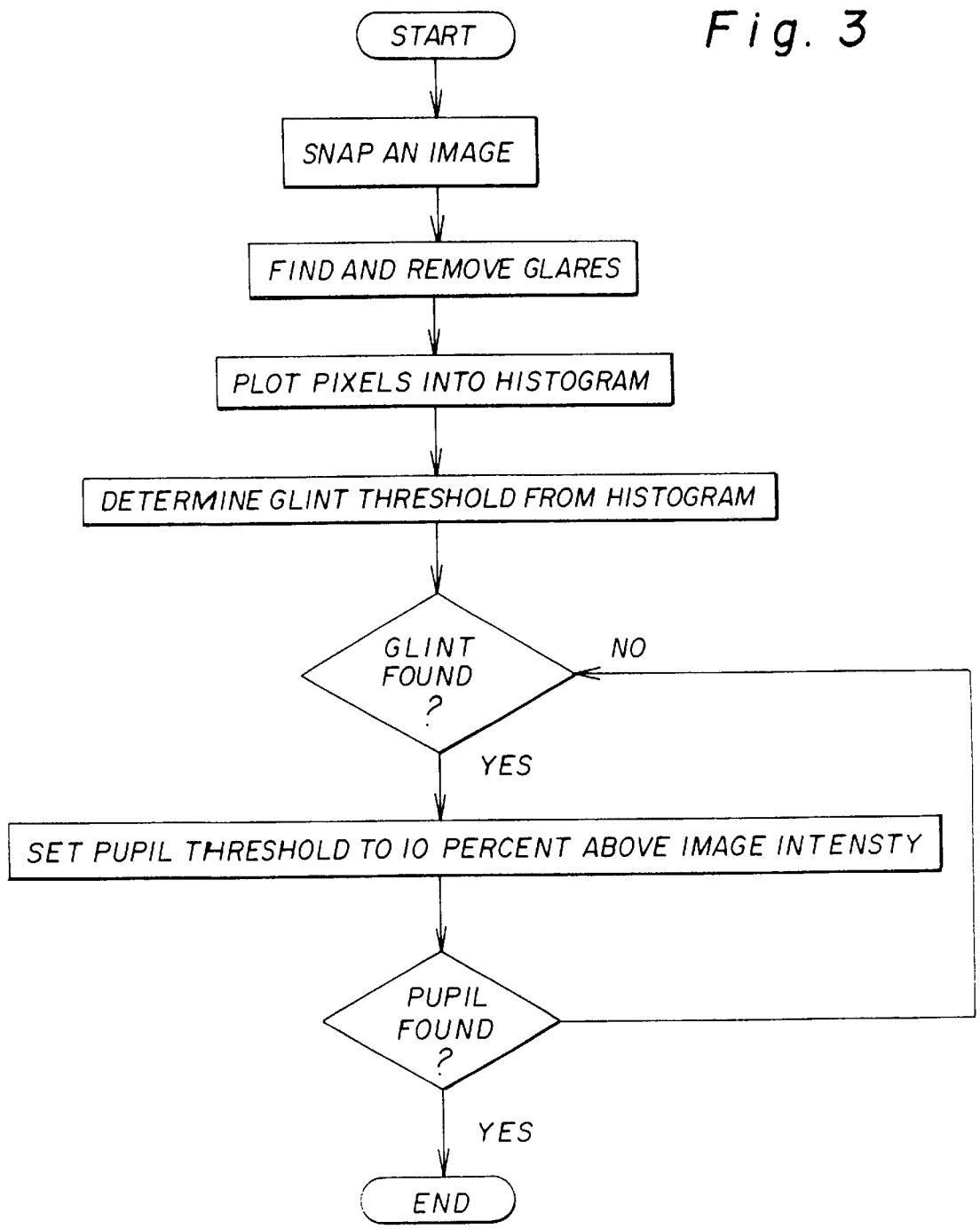

As mentioned earlier, the first step in using the system is to set thresholds; the basic procedure is outlined in FIG. 3. The object of this stage is to obtain the minimum intensity values of the glint and pupil so that the software may quickly identify both of these features during calibration and actual system operation.

In the first stage of threshold setting, the user looks directly back into the center of the camera, focusing on the image of the light emitting diode (LED) seen in the top mirror. The system snaps an image and maps it into memory.

Figure 4C:
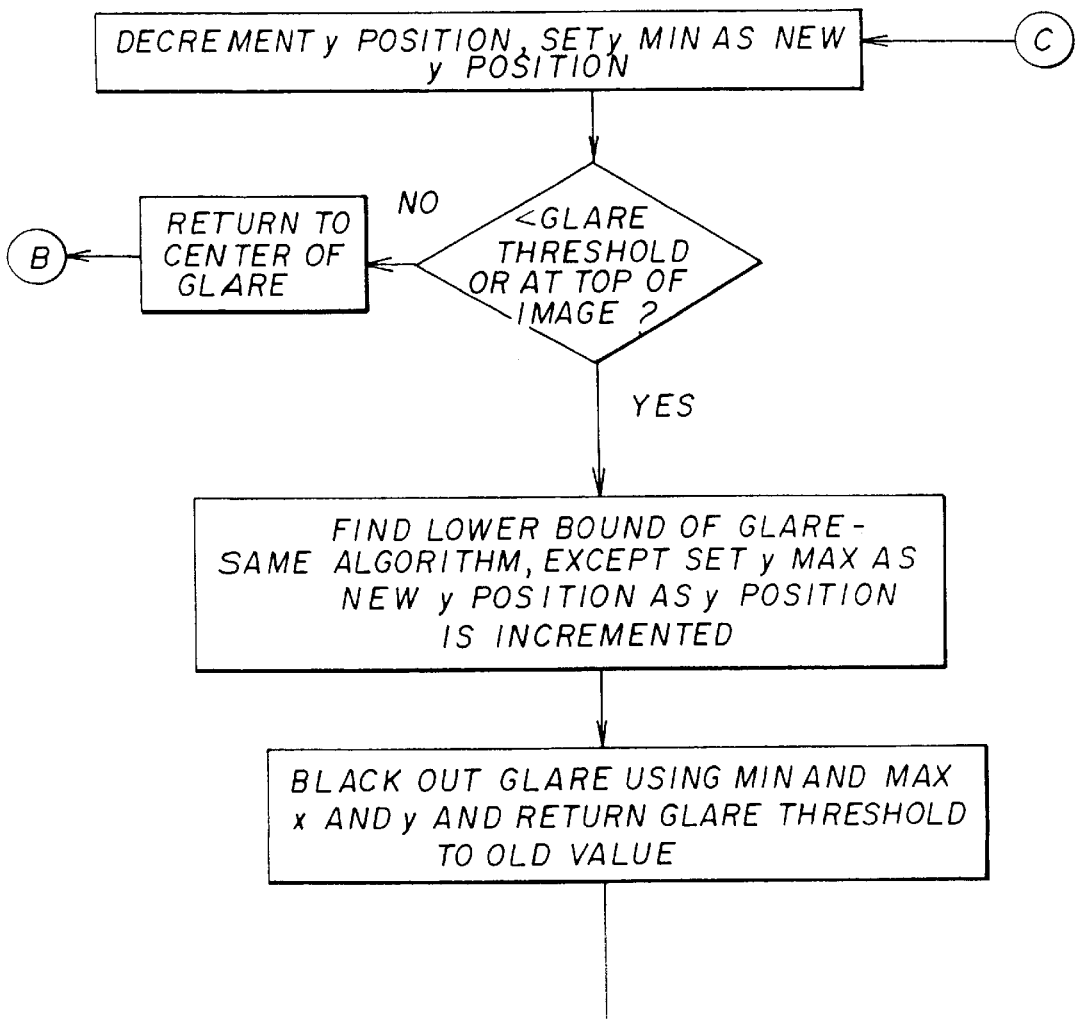
Figure 4D:
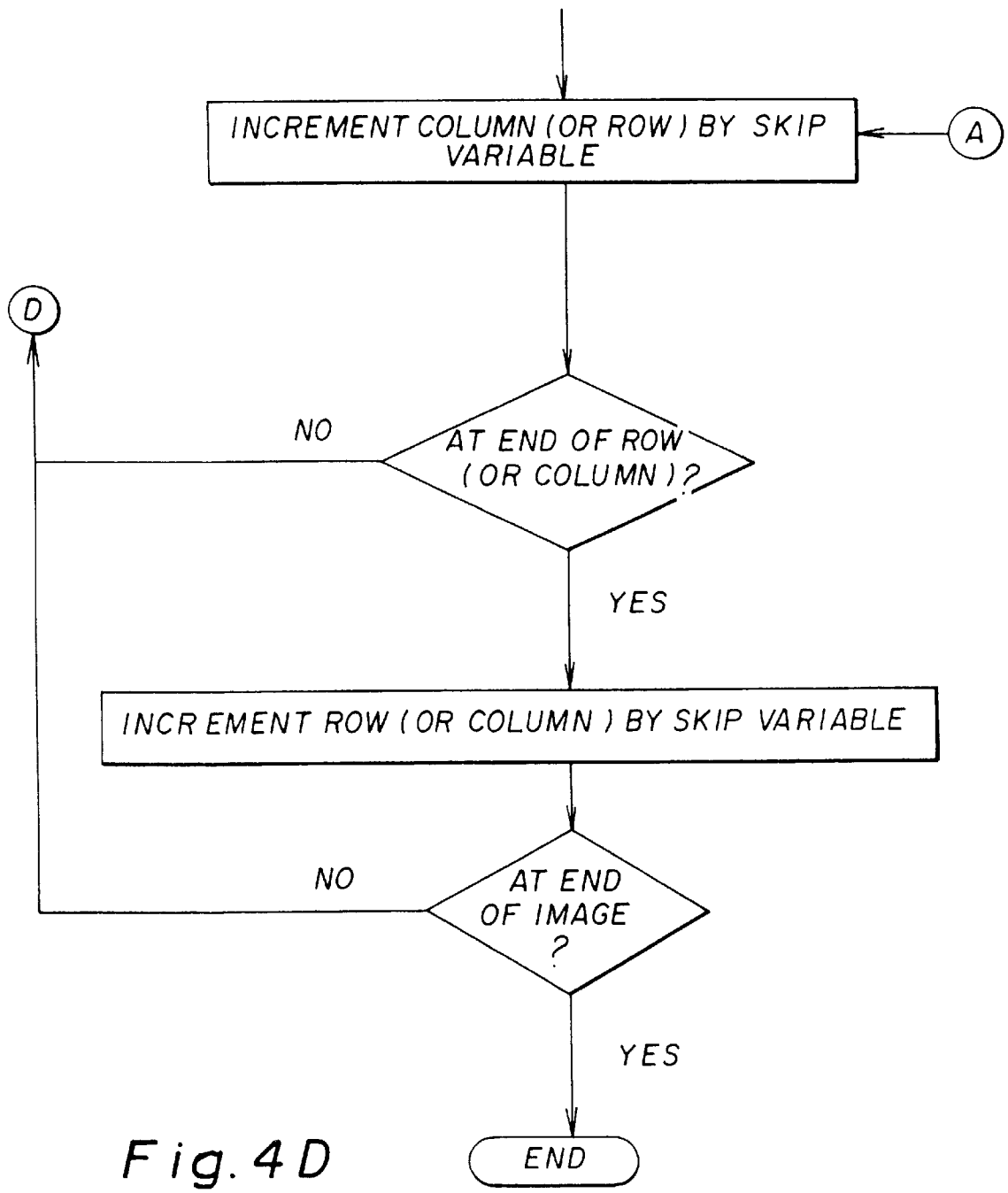

Once the image has been acquired, the system then checks if any glares are present using the flowchart shown in FIG. 4. The origin of the camera coordinate system is the upper-left corner of the camera image. The x coordinates increase as the system moves to the right. The y coordinates increase as the system moves down in the image. There are six parameters of interest. All of these parameters are set in or determined by HQ based on the user's desires or the camera setup. The first parameter, search scheme, specifies whether the software searches horizontally or vertically when trying to find the boundary of a glare. A third setting has the software perform two passes; one searching for glares horizontally first, then searching for the glares vertically. This last method maximizes the reduction of the glares but does slow system processing down. Two additional parameters specify how many lines to skip vertically and how many to skip horizontally as glare detection proceeds through the image. The more lines skipped, the less efficiently the system will remove the glares, but the less time will expire before the glare removal algorithm completes its task. Another parameter is the glare threshold, which is the intensity value above which a pixel could potentially be considered part of a glare. Another is the pixel length of the glare, which defines the number of pixels in succession that must be found greater than the glare threshold for a region of the image to be considered a glare. A glare generally has the same or higher intensity than a glint, but the glare is larger. Once a glare has been found, then the software will find a bounding rectangle for the glare. To determine this rectangle, the glint threshold is reduced by the last parameter, the adjust factor. This allows the software to remove the halo that typically accompanies a glare but is generally of a lower intensity than the glare. Once the threshold is reduced, then the system begins bounding the glare.

The system starts by moving to the right of the current sequence of pixels it believes to be part of a glare. The system checks each pixel as it advances to the right and stops its check when it either reaches the edge of the screen or finds a pixel whose intensity is below the glare threshold. The software then checks to the left, again advancing left until it either reaches the screen edge or finds a pixel whose intensity is below the glare threshold. The system then decrements its y value and checks to the left and right again. After an upper bound has been reached (the pixel value at the new y coordinate is below the threshold or the screen edge is reached), then the system increments its y value to find the bottom of the rectangle. During the checking, the overall minimum and maximum x values are stored. After the bottom of the rectangle is found, then the system has found both the minimum and maximum x and y values for the glare, so the glare is ready for removal, and the glare threshold is returned to its old value.

The system begins its search for the glares in the upper left-hand corner of the camera image. If any glares were found, then the system removes the glares by turning every pixel in the glare's bounding rectangle black. Glare removal is fast and has the advantage of decreasing the number of areas that the feature finding algorithms will query to attempt to identify the glint and pupil. Upon removing the glares, the system is now ready to attempt to set the thresholds (minimum intensity values) for the glint and pupil.

The first step is to determine a glint threshold. The system first makes a histogram of the intensity values for each pixel of the camera image. The intensity values range from 0 to 255, so there are 256 buckets. The number of pixels with an intensity value equal to the value of the bucket is stored in each bucket. Were this data to be plotted, several humps would appear. The lowest and largest hump would represent data that shows the intensity values of the face. The next highest hump would represent data for the bright eye and a spike near the highest intensity values would show an intensity value for the glint. To determine a starting threshold for the glint, the system begins at the end of the histogram (intensity value 255) and moves backward to each bucket, summing the value in each bucket. Once a value of twenty pixels is reached, the system sets the current bucket number to be the threshold for the glint.

Figure 5B:
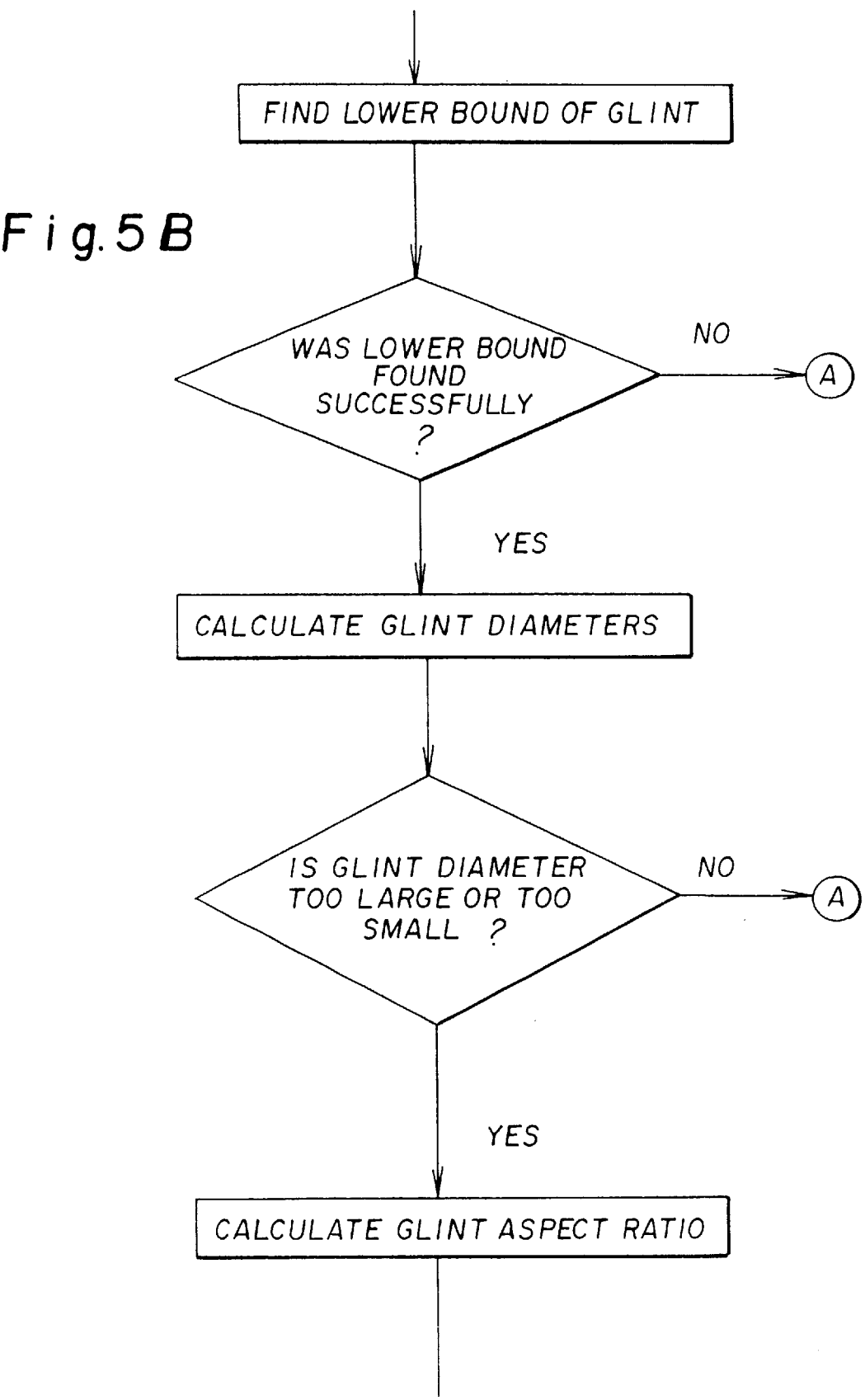
FIG. 5 shows how the glint center is determined.
Figure 5C:
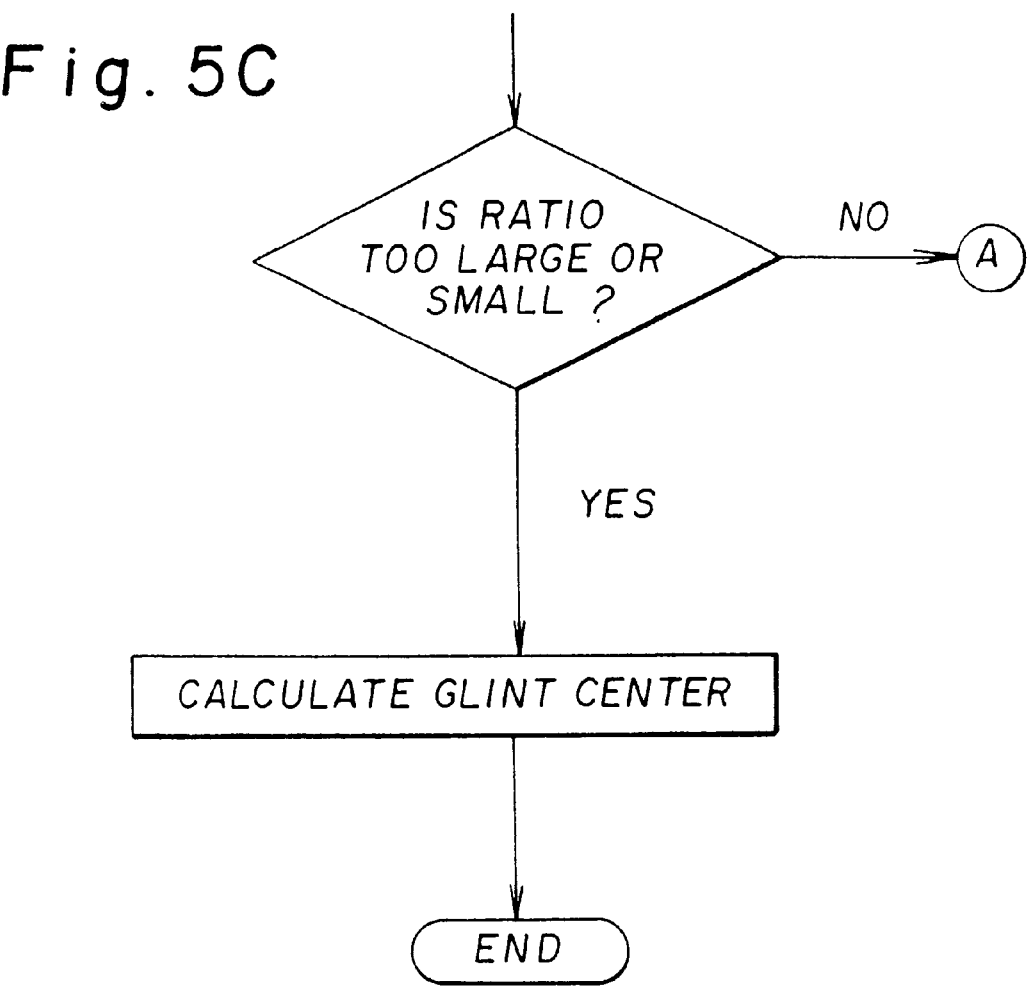

The next stage is to test this threshold by attempting to find a glint. The system will alter the threshold as errors occur in determining the glint's bounding rectangle. FIG. 5 shows a flowchart representing how a glint center is found. This is the same algorithm used to determine the glint center in calibration and runtime operation of the system.

The first step to finding a glint is to find a seed point, which is the pixel that serves as the starting point for attempting to find the glint's bounding rectangle. The system scans the search region to find the first pixel whose intensity value is greater than the glint threshold. If a seed is found but it is in the seed point memory array, which serves as a buffer containing the locations of all invalid glints, then it is ignored. The search region is either the entire image if the system is in a global search mode or a region of 180×180 pixels centered on the last valid glint if the system is in the local search mode.

Once a valid seed is found, then the system tries to find an upper bound on the glint. The system decrements its y counter by one pixel. It then tries to find the minimum and maximum x coordinates for the glint with the current y value. The system checks each pixel to the left and right and stops its check once it finds a pixel with an intensity value lower than the threshold. The system stores the overall maximum and minimum x coordinates of the glint's bounding rectangle for all lines checked. This process of checking each line is called filling. A filling error occurs when the system reaches the edge of the camera image and all the pixels checked are still above the threshold value. Once the first filling operation is completed, the system determines the x coordinate center of the line. This is the x value where the system will start its checks on subsequent filling operations as the y counter is changed. As the system decrements its y counter, it checks the intensity of the point at the new y and the previously determined x center. If the intensity is below the glint threshold, then the top of the glint has been found.

Next, the system tries to find a valid lower bound of the glint if the upper bound was found without error. This follows the same algorithm as far as filling is concerned. The only difference is that the y counter is being incremented.

If filling completes successfully, then the system determines the glint diameter, center, and aspect ratio. The diameters are calculated based on the maximum and minimum x and y coordinates. The aspect ratio is the ratio of the x diameter to the y diameter. All three of these values are checked against preset values and tolerances to ensure that a proper glint is found—that its shape belongs to a valid glint. For example, the glint's bounding rectangle should be approximately a square, so an aspect ratio that is too far above or below the value of one would signify an erroneous glint. If these three checks pass, then the system calculates the center of mass of the glint. As filling occurs, the system sums the number of pixels in the glint, and the x coordinates of valid glint pixels are summed as well as the y coordinates. The x coordinate of the center of mass is the x sum divided by the number of pixels and the y coordinate is the y sum divided by the number of pixels.

If the glint is not found due to a filling error, then the software performs the glint error handling routine as described below and attempts to find another glint. If no seed was found, then decrement the threshold by 10 units. If the glint threshold goes below the average image intensity, then snap a new image and restart the threshold setting procedure.

The glint error handling routine shown consists of a feature called seed point memory. This is a new innovation with the system that keeps it from bouncing between potential glints. Once a glint is found to be erroneous, then its bounding rectangle is added to the seed point memory. The system will then ignore any seed points that it finds in these regions while it attempts to analyze the present image. Once a new image is snapped, then this memory is cleared.

Next, the system sets an initial approximation for the pupil threshold. This value is set at 10 percent above the average image intensity.

The software then tests the threshold by attempting to find a pupil. The algorithm used is the same as the one used for the glint, except the system checks pixel intensities relative to the pupil threshold. If no pupil is found due to not being able to find a seed, then we are not looking at the correct glint. Perhaps the system is trying to bound some other reflection from the eye or a small glare escaped elimination. The software performs the glint error handling routine and tries to find a new glint. If the fill routines failed, then the pupil threshold might be too low, so try setting a higher threshold. The pupil threshold is increased by 10 percent, and the system tries to find the pupil again. If this step has already occurred, then we are searching around a bad glint so perform the glint error handling routine and try to find a new glint. The system then checks that there are not too many pixels in the pupil greater than the glint threshold. If this test fails, then the pupil found is not the true pupil, so the system performs the glint error handling routine and tries to find a new glint. If the pupil is found, then the system then tries to relocate the pupil after making the threshold 90 percent of the current average pupil intensity. The system uses a different routine to now find the pupil. This is the method used in the runtime operation of the system. This routine is essentially the same as the one used to find the glint, except the system will try to find the pupil several times before failing this section of the routine. Basically, if the pupil center determination fails, then the search region is adjusted based on the previously found max of the pupil; the new x starting position is set to the pupil x max and the y starting position is set to the pupil seed's y value plus 1. The initial search region for the pupil seed is a rectangle that is 30 pixels by 10 pixels and centered at 5 pixels above the potential glint's center. If the pupil cannot be found, then the glint is bad so perform the glint error handling routine and try to find a new glint.

Once both a glint and a pupil are identified, the system has now found valid thresholds. One of the improvements in the system is the use of dynamic thresholding, which means the threshold values used to define the minimum glint and pupil intensity are constantly updated as the system operates to provide more accurate bounds on the features during runtime. So, the software will now setup the minimum allowed pupil and glint thresholds, which are set to $2/3$ of the current threshold for the respective feature, ensuring that the minimum glint threshold is not below the current pupil intensity. Also, the system stores the current threshold to use as a reset point if the feature threshold ever gets adjusted too far. The system also stores the current glint intensity relative to pupil intensity to serve as an additional check during calibration and runtime. Lastly, minimum and maximum glint and pupil sizes are set based on the current features sizes.

An innovation added to this invention is the storage of the x and y offsets of the pupil center from the glint center that occurs as the user looks back into the camera. All of the mathematical models used in calibration and the discussions so far have assumed that the glint center is truly at the pupil center when the user looks back into the center of the camera; however, this is not the case for everyone. Thus, in subsequent determinations of the glint-pupil displacement, the system will subtract these stored offsets from the calculated x-y glint-pupil displacement before converting to the polar coordinates used by the calibration equations. This compensation more than doubles system accuracy for the typical user, granting them a consistent accuracy over the entire computer display. This increases the proportion of the population that can effectively use the system to control the GUI.

In the second stage of threshold setting, the user looks at the bottom of the computer display. The above algorithm is repeated, except the glint-pupil offset is not stored. This stage is necessary because the pupil is usually at a lower intensity when looking at the bottom of the screen than when looking directly back to the camera, and the pupil threshold needs to be set at the lowest possible valid value.

Figure 6:
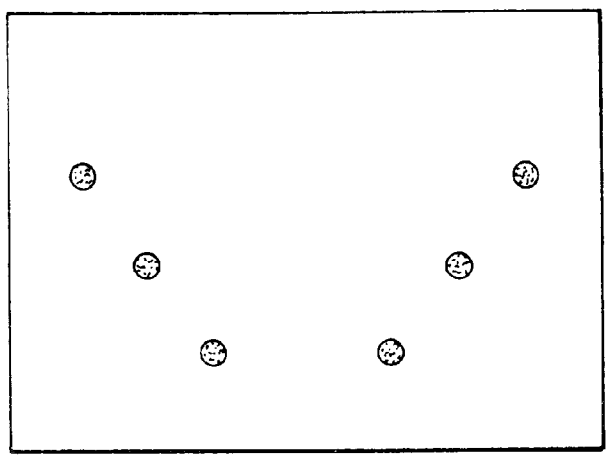
FIG. 6 shows the six point calibration layout.

Once the user has successfully completed threshold setting, they are ready to calibrate. Calibration is the process of determining the equations used to map angles and radii between the pupil and glint centers of the user's eye to radii and angles on the screen, with the origin of the coordinate system for the screen being just below the bottom center of the monitor's screen. To determine these equations, the user fixates on a sequence of calibration points shown on the computer display as either a dot or a picture of some type. Calibration is essential to achieving good accuracy with the system. No matter how well the system determines the pupil and glint centers, if the regression equations are faulty, then the accuracy will be poor. The current calibration algorithm sets up calibration points at fixed angles and radii from the origin of the monitor's coordinate system. The resulting configuration is a web of points expanding from just below the bottom center of the monitor's screen. Each radial line, a line of calibration points at a fixed angle from the monitor origin, performs its own linear regression for determining the equation used to map a radius between the pupil and glint center to a radius on the screen. Each arc of a constant radius performs its own linear regression for determining the equation used to map an angle between the pupil and glint center to an angle on the screen. These resulting equations allow the system to determine where the user is looking on the screen with a high degree of accuracy. FIG. 6 shows the current six point calibration method and these points grant the typical user an accuracy level of 5 mm and better at a standard viewing distance from the display.

The calibration procedure consists of the user fixating on each calibration point as the system shows each point one at a time. While the user fixates on the point, the software is snapping images and identifying glint-pupil displacements using the methods described above to determine the glint and pupil center. Note that these displacements are corrected by the glint pupil offset found during the first stage of threshold setting. The system tries to obtain ten valid displacements for each calibration point. The software then computes the median value for the ten samples and discards any samples that are too far away from the median; if the computed radius for a sample is more than one pixel from the median or if the computed angle for a sample is more than two degrees from the median, then the sample is considered erroneous. An average glint-pupil displacement is then determined by averaging the displacements of the remaining samples. If five or more samples are thrown out or ten valid samples cannot be obtained, then the system attempts to recalibrate the point. If the point fails calibration three times, then the software moves on to the next point and removes the calibration point from the linear regression algorithm.

As described above, the system determines a sequence of equations to map a particular glint-pupil vector to the screen. Once all calibration points have been completed, then the system uses a linear regression to calculate these equations. The system tries to find the best-fit linear line through the points corresponding to the different radii and angles that maximizes the correlation coefficient. If this value is too low or only two points went into the regression (a linear regression can always determine a line through two points), then the system will signal to the user that some of the points may need recalibrating if they wish to obtain better accuracy. The software has a method that allows the user to recalibrate only the points that caused the regressions to fail.

With calibration completed, the user may then enable the system through the HQ interface. If mouse emulation is enabled, then the mouse cursor will follow where the user is looking.

Figure 7:
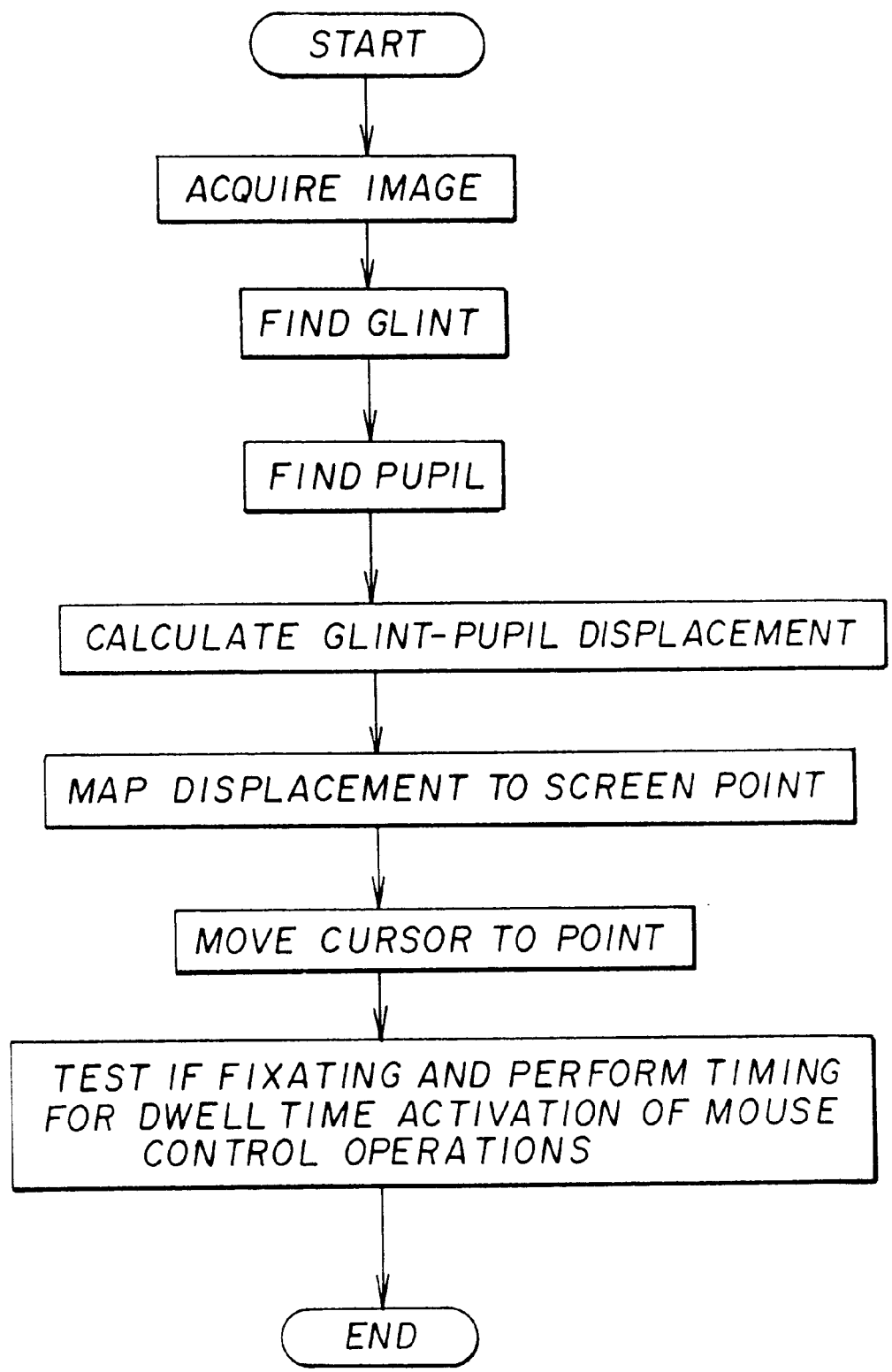
FIG. 7 shows how the system identifies features in the actual operation of the system.

To determine the user's point of regard on the screen and to effectively control the cursor, the software uses the algorithm shown in FIG. 7. HQ allows the user to specify the sampling rate—the frequency at which the system acquires an image and attempts to determine where the user is looking. A higher sampling rate burdens the system more, but delivers more data to the operating system. Even with the maximum sampling rate of 15 samples per second, effective control over the computer is possible with little degradation of system performance; however, when using a processor intensive application like a video game, the sampling rate might need to be reduced to improve performance. When the system is enabled, a timer starts that signals the system to acquire images at a frequency corresponding to the sampling rate. Once the image has been mapped into memory, the software uses the routines described above to determine the bounding rectangle for both the glint and the pupil. To speed up the search process, the system has two searching modes—local and global search. A global search attempts to find the glint at any region in the camera image. A local search centers the searching region on the previously determined valid glint; in essence, the system is assuming the user is sitting in the same position. Local searching greatly reduces the processing that must occur for the system to identify valid features, as a user's position typically does not vary much between successive frames.

In the event that a glint cannot be found, the system dynamically adjusts the glint threshold in an attempt to find the correct glint. If a filling error occurred, such as the system believing the glint was at the edge of the camera screen, then the system simply performs the glint error handling routine and jumps to a global search. If no seed was found, then the search region was exhausted, so it is time to adjust the glint threshold. If the bound on the bad glint resulted in a glint too big, then the threshold is increased by 5 pixel intensity units, which range from a value of 0 to 255. If the glint was too small, then the threshold is decreased. If neither of these conditions arose, then the system checks the search mode. If a local search is being conducted, then the threshold is decreased. If this occurs too many times, then the search mode is changed to global search. If a valid glint cannot be found globally, then the system simply waits. If three frames pass with no valid glint, then the threshold is reduced. If the threshold is reduced below the minimum threshold value for the glint, then tracking is failed for the image, and the thresholds are reset.

If a pupil could not be found, then the system jumps to a global search mode and performs the glint error handling routine and tries to find a new glint.

Once both features are found, then the system performs a few additional checks before calculating gaze position. First, the software checks the glint intensity relative to the pupil intensity. If this ratio is too small (as compared to the minimum set in threshold setting), then the glint detected is really most likely part of the pupil, so the glint threshold is increased and the system attempts to find a new glint. Next, the system checks that the glint center is not above the pupil center. During operation of a computer, the glint center will never be above the pupil center, so if it is, then an erroneous glint was found, so the glint error handling routine occurs, a global search for the glint is initiated, and the threshold is reduced. Lastly, the system checks the counter for the number of pixels in the pupil greater than the glint's threshold. If this is too high, then the glint is erroneous, so the same steps occur as for the glint center being above the pupil center.

If all features are found correctly, then the glint threshold is readjusted to be the current glint's intensity value. The x-y displacement is now calculated, and these values are adjusted by the glint-pupil offset found in threshold setting.

The system then performs a smoothing algorithm on the displacement. This has the advantage of removing some of the noise inherent in the calculation of the glint and pupil bounding rectangles. The software will compute a final displacement that is the average of the previous n displacements found, where n is the number of displacements to average over as set by the user in the HQ control interface. The higher the n, the less jitter that occurs in the data as the user fixates, but the slower the time in which the system can update the cursor position to reflect a change in the user's dwell area. This has the primary advantage of delivering better control over the cursor.

After the displacement has been smoothed, the system uses the regression equations to determine the user's point of regard as described in FIG. 8. The x-y displacement is converted to polar coordinates. The system first uses an angle regression based on all calibration points to get an approximation for the angle at which the user is looking. The system then uses this angle to determine which radial regression equations it should use to calculate the radius of the user's gaze on the screen from the monitor origin. The system finds the regression equations for the angles just above and below the angle previously determined. It then calculates the radius it thinks the user is looking at for both these equations. The system then interpolates between the two results, placing a higher weight on whichever equation is at the closest angle to the angle previously determined. The system then uses this radius to better determine the angle at which the user is looking by using the same method described above except the system is checking angular regressions now based on a fixed radius. Interpolation again occurs, and the system repeats the above sequence of determining the radius and angle to better approximate the user's point of regard. The system then converts the radius and angle of where the user is looking to Cartesian coordinates on the monitor.

These Cartesian coordinates then undergo a smoothing routine. This routine throws out any data that would place the new gaze position at a certain distance away from the previously determined gaze position. Essentially, the new gaze position would be considered as an erroneous point because it would be impossible for the user's gaze position to change by that much that fast. There is also a minimum movement check. If the new gaze position is only a small distance from the previous gaze position, then the mouse cursor's position will not be updated. This removes jitter in the cursor caused by noise in determining the glint-pupil displacement.

Using this smoothing and the above algorithms, the user now has effective control over the placement of the cursor in the GUI. The user can look at a certain position on the screen and have the cursor reach that position to an accuracy of about 5 mm or better for the typical user.

The system uses dwell time to provide the user with access to various mouse clicking actions. When the user fixates (focuses at a point on the screen and keeps the mouse cursor stationary) for a predetermined amount of time on the computer display, a red rectangle appears, centered on the point of fixation. This rectangle begins collapsing in on itself. The rectangle serves as a visual cue to the user that if they keep fixating at that point, they will be asked to perform a mouse control action at the point. When the rectangle reaches the end of its collapse by basically becoming a point at the user's position of fixation, then a window pops up near the center of the screen. The region around which the user was fixating appears magnified in this window as shown in FIG. 9. At the bottom of the window is an eye-gaze controlled button that closes the window if the user fixates on the button for a predefined length of time. The user then fixates in this window on where they actually wished to have performed a mouse action. A red rectangle again signals the user that continued fixation will cause another event to occur. If the rectangle reaches the end of its collapse, then a menu of six additional buttons appears in the window as shown in FIG. 10. Fixating on a button for a predetermined amount of time causes that button's action to be performed. The available actions include left mouse button drag, left mouse button single click, left mouse button double click, right mouse button drag, right mouse button single click, and right mouse button double click. A collapsing red rectangle again shows which button will be clicked if fixation continues. If the user is in the middle of a drag then all buttons stop the drag and then perform their set action, with the exception of the drag start buttons which only cease the dragging. The fixation times for all events described are user customizable to suit the different user's skill levels in operating the system as is the size of the zoom window and the factor by which it magnifies the area the user initially fixates at. The window size and the zoom level determine the amount of area on the screen that appears zoomed each time the zoom window opens.

The zooming feature is a recent addition to the invention and allows any accuracy concerns with the system to become moot. Even with an accuracy level of 2 to 3 millimeters, the user cannot consistently fixate on certain GUI control objects such as scroll bars and toolbar buttons when operating at a high resolution. The zooming feature provides a reliable means for activating a GUI control and accomplishing various tasks in the GUI environment. With this feature, individuals can effectively tap into the GUI interface using solely the eye.

The system is not limited to using the zooming feature and a menu for implementing click actions. If the user knows they are going to be only using certain actions, like left clicking, then the menu may be bypassed and different dwell times can activate the different clicking actions in the zoom window. Also, if the user is working in applications with large controls, as is the case in a children's game, then the zooming feature may be turned off, and dwell time activation of the different clicking actions can occur on the display.

When dwell time clicking is used, the collapsing rectangle goes through different phases to signal to the user the different actions that can be performed. The first stage is the collapsing red rectangle. If the dragging is enabled, then the rectangle will turn to a blue circle and continue its collapse. If the user looks away while the blue circle is shown, then they will start dragging what they were fixating on. If the user prolongs their fixation and allows the circle to reach the end of its collapse, then the system clicks once on where they were looking. Lastly, a green rectangle will appear and after a predetermined fixation time, the system will double click on where the user is fixating.

The colors used throughout this description are arbitrary and serve no purpose save delineating the different modes to the user.

The system may use an alternative method for clicking instead of the dwell time. If the operator still has some use of their hands, then pressing a single key on the keyboard will make the system click where they are looking. This has the advantage of greatly speeding up the clicking process. The key on the keyboard works like a mouse key, pressing the key twice quickly performs a double click.

This variety in the clicking mechanisms allows the eye-gaze system to be optimized for each user—the user interfaces with the GUI in the most efficient method that suits their particular needs.

An eye-gaze direction detector and method has been disclosed that provides a means by which a human operator, including a paraplegic, can interface directly with a computer by eye gaze alone in an efficient, reliable, and flexible manner that is both very fast and has a high degree of screen resolution. All material set forth should be considered illustrative and not as the limiting sense. The invention is to be interpreted within the spirit and scope of the following claims.

APPENDIX

This appendix contains an in-depth description of the functionality of the HQ control interface software and provides an introductory user's guide.

This appendix is considered part of the specification of the invention.

CHAPTER 1
An Introduction to ERICA

Overview

ERICA, the Eye-gaze Response Interface Computer Aid, is a computer workstation configuration which achieves the function of an eye-controlled mouse. By using advanced imaging hardware and software, the system tracks movement of the eye by monitoring optical features which may be translated to a lookpoint. The lookpoint, or point of regard, represents the location of the user's gaze on the screen. In this way, through the sole use of the input from the user's eye, the ERICA system can execute an unlimited number of functions. In particular, the ERICA system is configured to record the point of regard and ocular characteristics, such as pupil area, as a function of time and position on the computer display. The ERICA system can also grant complete control over the computer using only the eye.

Theory of Operation

The goal of an eye-gaze system is to determine the point at which the user is looking. The system monitors the position and movement of the eye in order to execute the software commands. The eye image has two significant features used in lookpoint position detection, the glint and the bright-eye.

*Glint*

The glint is a bright point of infrared light which has been reflected off the corneal surface of the eye. This appears on the TV monitor as a small, intense area of light. The position of this feature changes minimally relative to the center of the corneal curvature, allowing the glint to provide a fixed reference point for eye direction.

Chapter 1 An Introduction to ERICA

*Bright-Eye (Pupil)*

The bright-eye is a feature in the image corresponding to infrared light absorbed and reflected from the back of the eye (the retina) through the pupil. The bright eye appears in the monitor as an area of infrared light, larger and less intense than the glint, but more intense than the "dark" image of the surrounding iris. The position of the bright eye moves in the camera image field, following the motion of the eye.

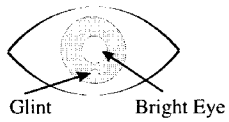

Figure 1.1: Image of the eye with the Glint and Bright Eye labeled.

The relative centers of these two optical features serve as the endpoints of a vector which indicates the direction of the user's point of regard. The relationship between this vector and the lookpoint is not generic. Each individual's eye has unique features which cause this relationship to vary. A calibration step is required to determine the exact relationship between vector and lookpoint so that an accurate lookpoint will be measured for a particular user.

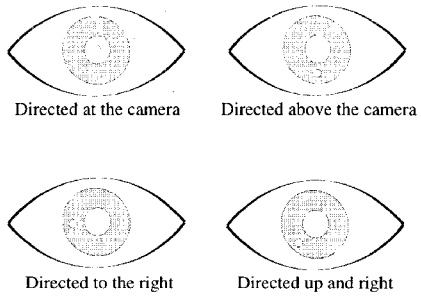

Figure 1.2: Determining Lookpoints using the Glint and Bright Eye.

CHAPTER 2
Setup

Required System Components

- *Pentium computer:* running Windows 95.

- *Matrox Meteor Video Capture Board:* Receives a signal from the camera which is then turned into a digitized image for the computer.

- *Hitachi CCD Camera and LED:* The primary device through which the information about the user's eye is conveyed to the computer. The camera is positioned beneath the computer monitor and must be focused on the eye. At the center of the camera lens is a Light Emitting Diode (LED), which projects low-power infrared light. This light is reflected from two mirrors and then onto the eye. Infrared light is harmless and invisible to the human eye, so the light does not interfere with operation of the system. The camera can locate the lookpoint by filtering out all but the infrared light.

- *TV monitor:* Displays the image which the camera is receiving. This enables the user to verify that the eye is within the field of the camera.

- *Camera/Mirror Platform:* A product of ERICA Inc.

ERICA Hardware Setup

The Pentium computer should be set up and installed according to the manufacturer's directions for connections to a monitor, a keyboard and a mouse. In addition, the camera and the TV monitor must be connected to the computer. The computer monitor is placed on top of the camera/mirror box. The TV monitor is positioned so that the user's eye can be easily positioned and focused.

The power supply should be connect to the back of the camera. The box should also be plugged into the power outlet. The BNC cable should be connected from the input of the TV monitor to one side of the splitter on the back of the camera. The BNC end of the frame grabber should be connected to the other end of the splitter. The other end of the frame grabber cable should be connected to the fram grabber card on the back of the tower.

☞ Lighting Tip: Fluorescent lighting is strongly recommended. Incandescent lighting gives off infrared which interferes with the system.

CHAPTER 3
ERICA HQ's User Wizard

To begin using the ERICA system, power up and double-click on the ERICA HQ icon. For users who are new to the system, HQ provides a sequence of dialog boxes that provide you with step-by-step instructions. This sequence is known as the User Wizard. Upon completing the User Wizard sequence, ERICA is ready for use with applications. If this features is not enabled, you may enable this feature by selecting *Start Options* from under the Control pull-down menu. In the dialog box, check *User Wizard* and click *OK*.

User Wizard

The User Wizard provides the necessary instructions to a beginner for the setup of ERICA. The following section elaborates on the functions and options presented in the opening dialog sequence.

 You can choose to skip this section or any part of it by choosing *Cancel* at any time. You may execute any of the functions prompted by the dialog boxes by using the menus and the icons in the General Menu.

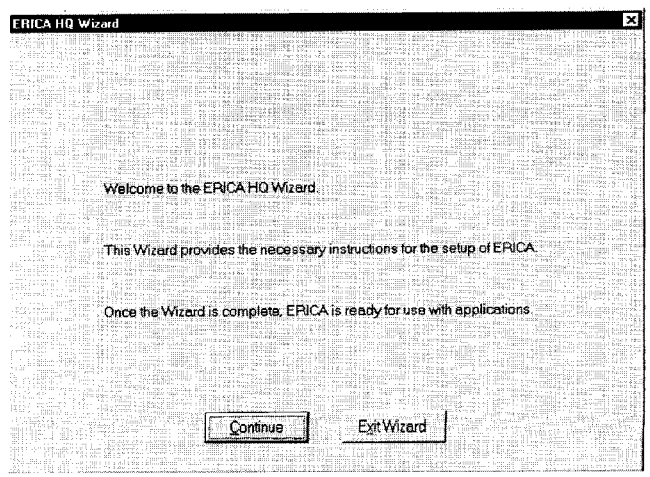

Figure 3.1: ERICA HQ Welcome Dialog.

- Step 1: Enter your Test Subject ID.

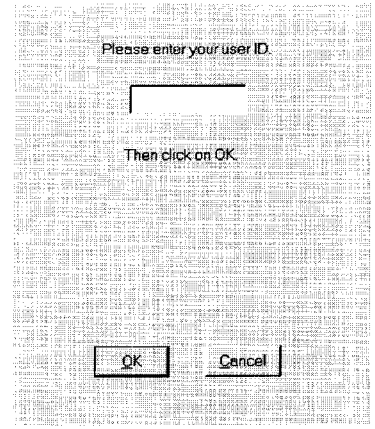

Figure 3.2: Test Subject ID Dialog.

- Step 2: Focus image of eye on the TV monitor.

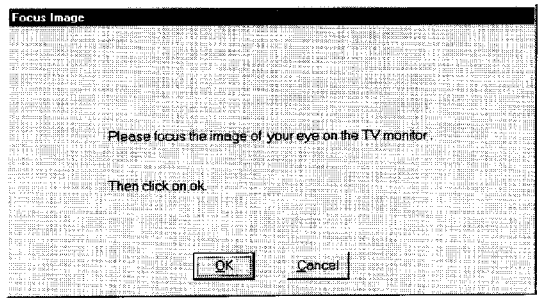

Figure 3.3: Focus Image Dialog.

Sit comfortably and position your head against the chair's headrest to minimize movement. Once comfortably seated, adjust the top mirror until one eye is centered on the TV monitor. Finally, turn the focus knob and/or adjust your distance from the camera until the image of your eye appears clear and sharp on the TV monitor.

☞ As you center your eye on the TV monitor, remember the effect of mirrors. If you need to move the image of your eye to the right, you must move your body to the left and vice versa.

- Step 3: Set Thresholds by looking at the large red dot at the bottom of the screen. The window will automatically close when thresholds have been set.

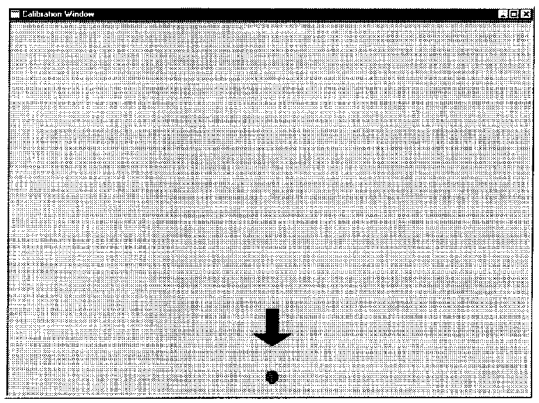

Figure 3.4: Set Thresholds Window.

- Step 4: Have you used the ERICA system before?

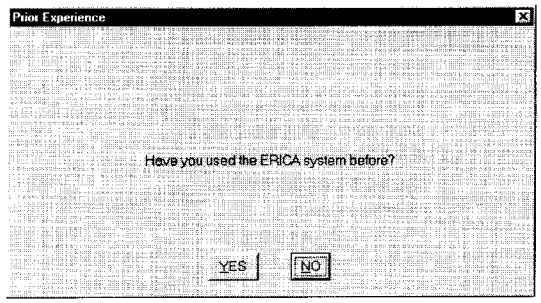

Figure 3.5: Prior Experience Dialog.

If *No*, you will continue with Step 5.
If *Yes*, you will continue with Step 6.

- Step 5: Would you like to Load a Calibration or Recalibrate?

☞ In order to increase accuracy, it is strongly suggested that you always recalibrate.

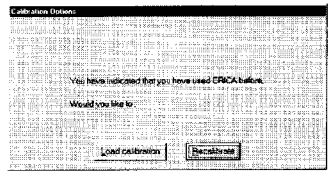

Figure 3.6: Calibration Options Dialog.

If you choose to *Recalibrate*, continue to Step 6.
  If you *Load Calibration*, you will be presented with a file browser in order to choose the desired calibration file.

- Step 6: Calibrate by looking at the sequence of points which appear on the screen. Close the window when you are finished.

☞ Do not rush this step! Look at each point util the calibration point moves.

☞ Blinking will not affect calibration data.

☞ If you are having trouble, make sure the image of your eye is in focus on the TV monitor. If it is not, try adjusting your position in relation to the camera.

Chapter 3                                                                  User Wizard ☞ If you hear a beeping sound, ERICA is having difficulty finding your glint. Be patient and repeat the calibration series.

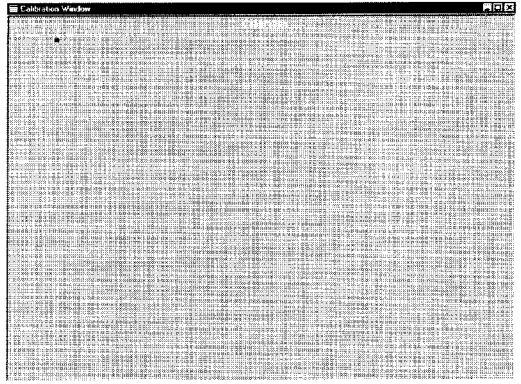

Figure 3.7: Calibration Window with Sample Calibration Point.

☞ If ERICA has recorded multiple calibration samples that fall too far from the actual point, ERICA will attempt to recalibrate that point. The part will flash.

The system is now fully calibrated. Any automatic settings that are set to excute following calibration will be performed.

A User's Guide to ERICA 3.5

CHAPTER 4
*ERICA HQ Menu Structure*

ERICA HQ provides the user with a control panel of functions that operate the eye-gaze system. Functions can be accessed by selecting the icons in the tab menus or from the pull-down menus. These menus access many of the same functions that may have been initialized in the opening dialog.

Control Panel

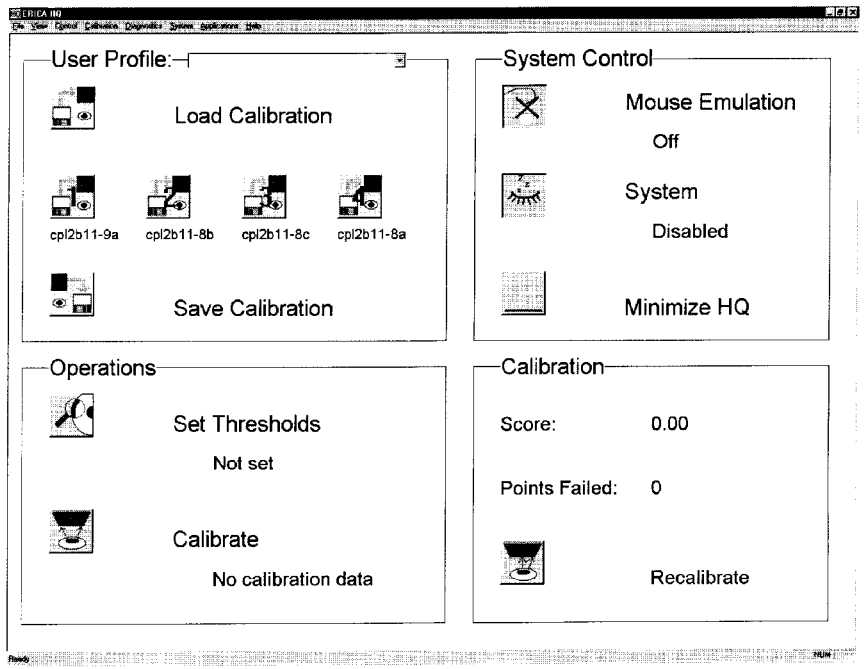

Figure 4.1: Control Panel in ERICA HQ.

Chapter 4                                                                      ERICA HQ Menu Structure

User Profile

- *User ID:* If you have completed the User Wizard, your user ID should appear in the space provided. Otherwise you may type in another user ID, or you may browse through the saved IDs by selecting the arrow to the right of the space. User IDs enable the ERICA system to handle the different calibrations and settings for multiple users.

- *Load Calibration Icon:* If the you have already performed and saved a past calibration, enter your ID in the space and click on the icon to load this calibration. You must set thresholds before you can you can load a calibration file.

☞ The user ID must be specified to load a previous calibration. If not, you will get a warning as displayed in figure 4.2.

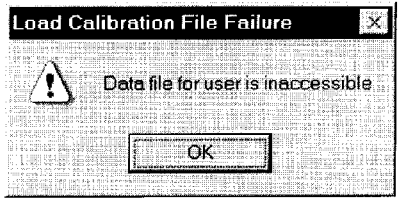

Figure 4.2: Warning Dialog to specify a user.

- *Recent Calibration Icons:* The four most recent calibrations are displayed for easy access. They are ordered from one to four, where one is the most recently used calibration. The name of the saved calibration is listed beneath each icon.

- *Save Calibration Icon:* Click this icon to save a current calibration under the current user's ID.

☞ You must calibrate before you can save any calibration data.

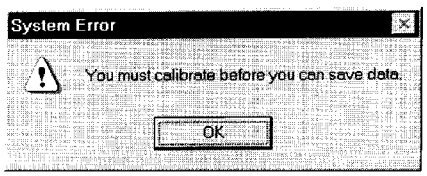

Figure 4.3: Warning Dialog to calibrate before saving data.

System Control

- *Score:*

The score is a rating of the success and accuracy of the current calibration. Scores range from zero to 100, with 100 being the maximum score. A score of 95 or lower will be highlighted in red. Such scores are recommend to be recalibrated.

- *Points Failed:*

This number represents the number of points that failed in calibration. If you click the recalibrate icon, you can recalibrate just these points.

- *Recalibrate:*

Recalibrate any failed points.

Pull-Down Menus

File

Figure 4.6: File Pull-Down Menu

- *New User*

This option allows you to restart the opening dialog sequence in order to calibrate and set up the ERICA system for a new user.

- *Save User*

This option will save the current calibration under your specified user ID.

- *Exit*

Selecting this option will close ERICA HQ.

View

Figure 4.7: View Pull-Down Menu

- *Status Bar*

The Status Bar is the gray bar the runs along the bottom of the HQ window. Most of the time, it will display the word *Ready* in the lower left-hand corner. It will also display helpful messages when certain options have been selected from the Pull-Down Menus. A ✓ indicates that the status bar is enabled.

Control

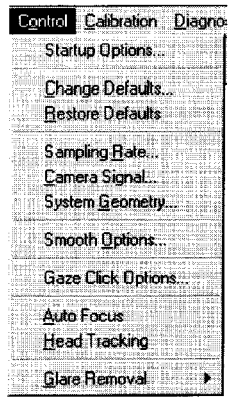

Figure 4.8: Control Pull-Down Menu

The Control menu options access many of the same functions that may have been initialized in the Opening Dialog Sequence.

- *Startup Options...*

When Startup Options is selected, a new window will open in HQ entitled HQ Startup Options. This window contains setup and calibration options that are available when HQ is opened. By default, the options *Set Thresholds, Then Calibrate* and *Large Calibration*, will all be checked. This means that when ERICA HQ is executed, it will automatically prompt the user to *Set Thresholds* and then perform a *Large Calibration*.

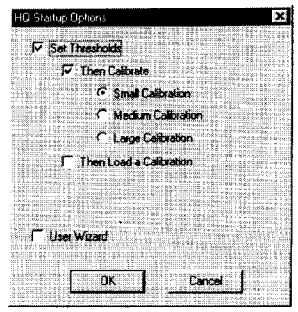

Figure 4.9: The Startup Options

*Set Thresholds* - When this item is checked, ERICA HQ will prompt the user to set the system thresholds at the start of HQ execution. If this item is checked, the user has the choice of either leaving both Calibration options blank and skipping that procedure, or choosing either to *Calibrate* or to *Load a Calibration*.

> *Calibrate* - If this item is checked, ERICA HQ will prompt the user to set the system thresholds and then calibrate the system. You may choose between either a *Small Calibration* or a *Large Calibration*.

☞ The difference between a *Small Calibration* and a *Large Calibration* is the number of points that are presented to the user in order to calibrate the system. A *Small Calibration* takes less time, but is also less accurate than the *Large Calibration*. A *Large Calibration* is always recommended for greater system accuracy.

> *Load Calibration* - This option tells HQ to load a previously saved calibration when HQ is opened. When this item is checked, a box will appear for the user to enter the desired User ID.

☞ A valid User ID must be entered in the box for this option to perform correctly.

*User Wizard* - If this selection is checked, HQ will guide the user through a step-by-step calibration process at the beginning of HQ. This process is detailed in Chapter 3 of this instruction manual.

☞ The ERICA system will not operate if thresholds have been set, but calibration
   has not been performed.

- *Change Defaults...*

You may change the system defaults by selecting this item. This option is password protected.

- *Restore Defaults*

Selecting this option will restore all settings to their default values.

- *Sampling Rate ...*

The Sampling Rate is the frequency at which ERICA attempts to estimate the user's gaze point. We suggest the maximum setting of 15 frames per second. For more details, see page 4.4.

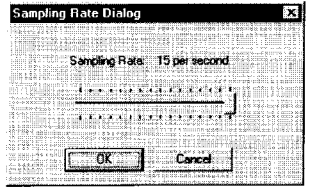

Figure 4.10: Sampling Rate Dialog.

- *Camera Signal ...*

☞ Making an adjustment to the offset or gain may cause system inaccuracy in the detection of glares and require readjustment of the Glare Threshold value. Therefore it is strongly recommended that you not change these values.

Offset (0-255)
    This operation allows you to adjust the brightness of the image by adjusting the DC offset of the incoming camera signal. The default setting is 128.

Gain (0-255)
    This operation allows you to adjust the black and white contrast of the image. The default setting is 30.

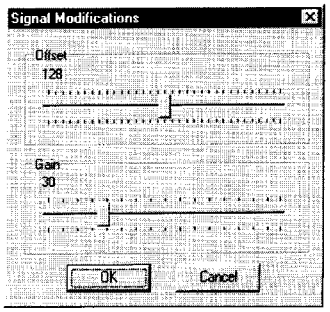

Figure 4.11: Signal Modifications Dialog.

- *System Geometry ...*

LED Separation Fraction
    The LED Separation Fraction informs ERICA HQ of the position of the LED in relation to the monitor. The value entered is the distance from the LED (camera lens center) to the bottom of the display screen divided by the screen height. The default setting is 0.35. For an alternative method of adjusting the Separation Fraction, see page 4.8.

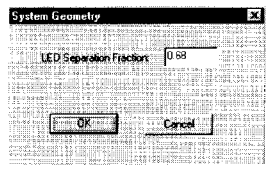

Figure 4.12: System Geometry Dialog.

- *Smooth Options ...*

As Chapter 3 explains, smoothing is a process in which the current screen point is averaged with several previously estimated gaze points. This reduces cursor jitter due to digitization artifacts and ensures that the screen pointer stays largely fixed when the user is looking at a single point on the screen.

Smooth filter point count (1-30)
    This is a count of the number of points that are included in each smoothing average. We recommend a count of at least 1.

Throw out distance
    The throw out distance is the maximum distance (in screen pixels) from the current screen point that the previous gaze points must fall within. Points outside this distance will be excluded in the smoothing average. An optimal throw out distance is 40 pixels.

Minimum movement distance
: This is the minimum distance (in screen pixels) between the current point and the smoothing averaged point. Smoothing will not be executed for distances less than this distance. We recommend a value of 5 pixels.

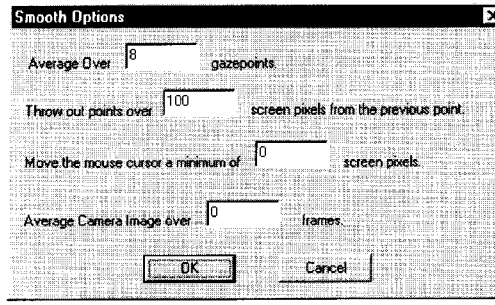

Figure 4.13: Smooth Options Window.

Camera Frame Average
: This averages glint and pupil relative distance over several frames to decrease cursor jittering. The recommended optimal value is 5.

- *Gaze Click Options...*

When you select this option a new window will open in HQ entitled "Gaze Click Options". Within this window will be one option named *Enable Gaze Clicking*. When the item is checked, the window will present you with a number of features shown in the figure below:

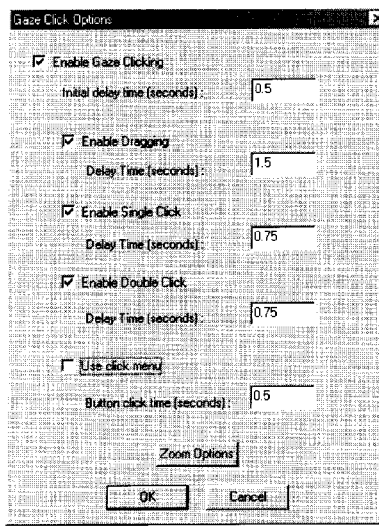

Figure 4.14: The Gaze Click Options window

*Initial Delay Time* - The *Initial Delay Time* is the duration of time before the red box starts collapsing when the user's gaze focus is stationary. The default value is .5 seconds.

*Enable Dragging* - This option enables you to click-and-drag items across the Windows environment. A ✓ indicates that *Dragging* is enabled. In the Windows environment, the ERICA system will display a two-stage collapsing box. The first stage takes place between the start of the collapse and halfway to a fully collapsed box. At this point, the collapsing box will become a circle and continue to collapse. When the circle is blue, you may drag the selected object by shifting your gaze. When you focus your gaze on the point where you would like the object dragged drag to, the box will collapse again. At the halfway point of this collapsing box, the item will automatically be released.

> *Dragging Delay Time* - This is the time it takes after the *Initial Delay Time* for the box to reach the blue halfway point. If the *Initial Delay Time* is set at .5 seconds, and the *Dragging Delay Time* is set for .5 seconds, than it will take 1 second after the cursor is stationary before you can drag an item.

*Enable Single Click* - This option enables the user to register single clicks through the ERICA system. A ✓ indicates that *Single Click* is enabled.

*Single Click Delay Time* - This is the time it takes after the last option for a single click to occur. If *Dragging* is enabled, then the total time to click is equal to the *Initial Delay Time* plus the *Dragging Time* plus the *Click Time*. If *Dragging* is not enabled, then it is merely the time after the *Initial Delay Time*.

*Enable Double Click* - This option enables the user to register a double click through the ERICA system. A ✓ indicates that *Double Click* is enabled.

*Double Click Delay Time* - This option operates identically to the above delay time options.

*Use Click Menu* - Instead of using the above clicking system, HQ also has a set of menu options that can be accessed whenever the user fixates his or her gaze in an area for a pre-determined amount of time. The menu is shown below in figure 4.15.

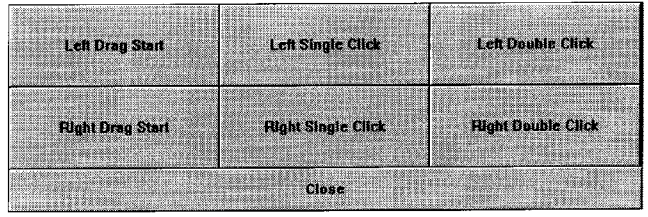

Figure 4.15: The Click Menu

*Zoom Options Button* – When the *Zoom Options* button is clicked, a new window will open as appears in figure 4.16. This window will enable you to customize the zoom options that HQ provides. The lower half of this window contains a preview space where the user may view a zoom example while customizing the features.

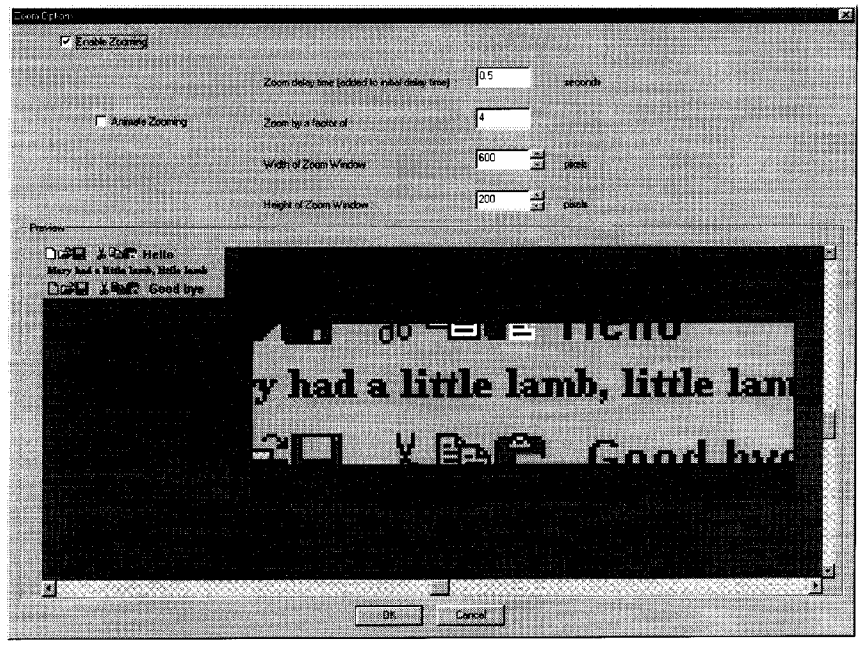

Figure 4.16: Zoom Options

*Enable Zooming* - When this item is checked, zooming will be enabled. Zooming occurs whenever the user fixates on an area for a certain amount of time and the system is enabled. HQ will take the area around where the click originated from and zoom it in a provided window space. The user may then click on any area within the zoom window, enabling a much higher accuracy.

*Animate Zooming* - When this item is checked, the zoom window will grow out of the collapsing rectangle.

*Zoom Delay Time* - This is the amount of time in seconds that must elapse after the initial delay time before zooming takes place.

*Width of Zoom Window* - This option enables the user to specify the zoom window width.

*Height of Zoom Window* - This options enables the user to specify the zoom window height.

- *Auto Focus*

Using this selection, you may either enable or disable the automatic focusing of the camera by ERICA. This function should be turned off if you are manually focusing the camera using the focusing knob on the ERICA system. A ✓ indicates that *Auto Focus* is enabled. In addition, to turn *Auto Focusing* on, a switch in the back right of the box must be flipped down. To use the knobs, the switch must be flipped up.

- *Head Tracking*

The ERICA system is capable of automatically tracking the user's head to keep the user's eye within the camera range. Toggling this feature enables you to have a small amount of lateral movement without disrupting the ERICA system. A ✓ indicates that Head Tracking is enabled.

- *Glare Removal*

ERICA HQ is designed to detect and remove glares that are a result of glasses worn by the user. In general, contact lenses do not produce such glare and should not have an effect on determining glint or bright eye position. Glares cause false glint and pupil detection and defeat the gaze find algorithm. If glasses are not being worn, this option can be disabled.

Glasses have a radius of curvature much larger than the white part of the eye (the sclera). This results in a glare that is larger than the glint and frequently of greater intensity. A glare removal algorithm is designed to blank these high intensity, large areas. When glares which fall on the glint and/or pupil are removed, however, the respective eye feature is also removed. So it is imperative that the glares not rest on top of the pupil or glint. High IR sources external to the system such as a window or incandescent lights can cause glares that are difficult for the system to accommodate. Thus high IR sources should be eliminated if possible.

Automatic Glare Detection

By default, automatic glare detection is enabled. A ✓ indicates that automatic glare detection is enabled. *Enabled* and *Disabled* options appear gray, but a ✓ indicates glare detection by the system. A ✓ by *Enabled* indicates that every detected glare will be removed.

Figure 4.17: Automatic Glare Detection Enabled.

☞ After Enabling *Automatic Glare Detection*, you should *Set Thresholds* again to ensure system accuracy after toggling *Auto Glare detection*.

To disable *Automatic Glare Detection*, click on the menu command. Then the *Enabled* and *Disabled* functions can be selected manually.

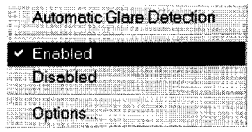

Figure 4.18: Manual Selection of Glare Detection.

☞ After Enabling *Glare Detection*, you should *Set Thresholds* again to ensure system accuracy after toggling *Glare detection*.

Options

Pixel Length (pixels): Minimum number of pixels of a bright spot on the image for the system to consider the spot a glare. We suggest a value of 2 pixels.

Glare Threshold: Minimum intensity for a pixel to be considered part of a glare. We recommend a setting of 200.

Adjustment Factor: The amount by which the glare threshold is adjusted once a glare is detected. We suggest that this value remain at 80. This allows the halo around a glare to be removed as well.

Search Scheme: These options are intended for advanced users. You may choose whether you would like the ERICA system to search for glare *Vertically, Horizontally* or both ways. You also have the option of selecting how many lines at a time these searches are done. Choosing a search scheme of both and a search of 1 line vertically and 1 line horizontally will result in maximum glare elimination, but performance will suffer. Thus, we recommend a search scheme of horizontal and 2 vertically, 2 horizontal for increased performance.

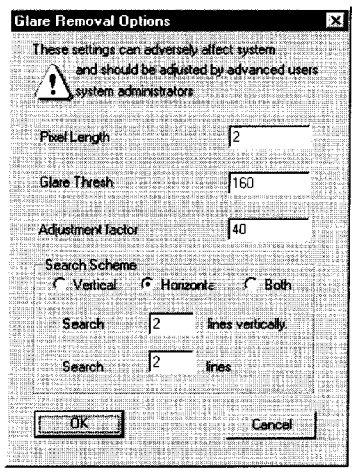

Figure 4.19: Glare Removal Options Dialog.

Chapter 4　　　　　　　　　　　　　　　　　　　　　　　　　　　　ERICA HQ Menu Structure

Table 4.1: ERICA HQ Control Functions.

| Control Function | Default Value | Range | Reasons for changing default value |
|---|---|---|---|
| Sampling Rate | 15 frames/sec | 0-15 frames/sec | Applications requiring system efficiency |
| *Camera Signal Options* | | | |
| Offset | 128 | 0-255 | Adjusts brightness of image |
| Gain | 30 | 0-255 | Adjusts contrast of image |
| *System Geometry* | | | |
| LED Separation Fraction | 0.35 | 0-1 | None |
| *Smooth Options* | | | |
| Smooth filter point count | 1 points | 1-30 points | Adjusts number of points used in cursor placement |
| Throw out distance | 40 pixels | 0-2000 pixels | May help eliminate "cursor jitter" |
| Minimum movement distance | 10 pixels | 0-500 pixels | May help eliminate "cursor jitter" |
| *Glare Removal Options* | | | |
| Glare Length | 2 pixel | 0-640 pixels | None |
| Glare Threshold | 200 | 0-255 | Requires adjustment if changes are made to camera signal options |
| Adjustment Factor | 80 | 1-1000 | None |

Calibration

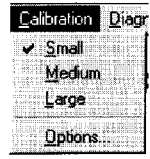

Figure 4.20: Calibration Pull-Down Menu.

- *Small*

When this selection is checked, HQ will perform a *small* calibration when the Calibrate button is clicked.

- *Medium*

*I* When this selection is checked, HQ will perform a *medium* calibration when the Calibrate button is clicked.

- *Large*

When this selection is checked, HQ will perform a *large* calibration when the Calibrate button is clicked.

☞ The difference between a *Small Calibration* and a *Large Calibration* is the number of points that are presented to the user in order to calibrate the system. A *Small Calibration* takes less time, but is also less accurate than the *Large Calibration*. A *Large Calibration* is always recommended for system accuracy.

• *Options...*

The *Options* menu will enable the user to set the different calibration options that are available. Calibration can be a long and uninteresting process, especially for children. Thus ERICA provides alternate calibration markers from the tradition target. The user may change colors, use a smiley face, or use his or her own bitmap file for calibration. Other options are included so that the user may find what works best for the himself or herself. These options can be seen in figure 4.21.

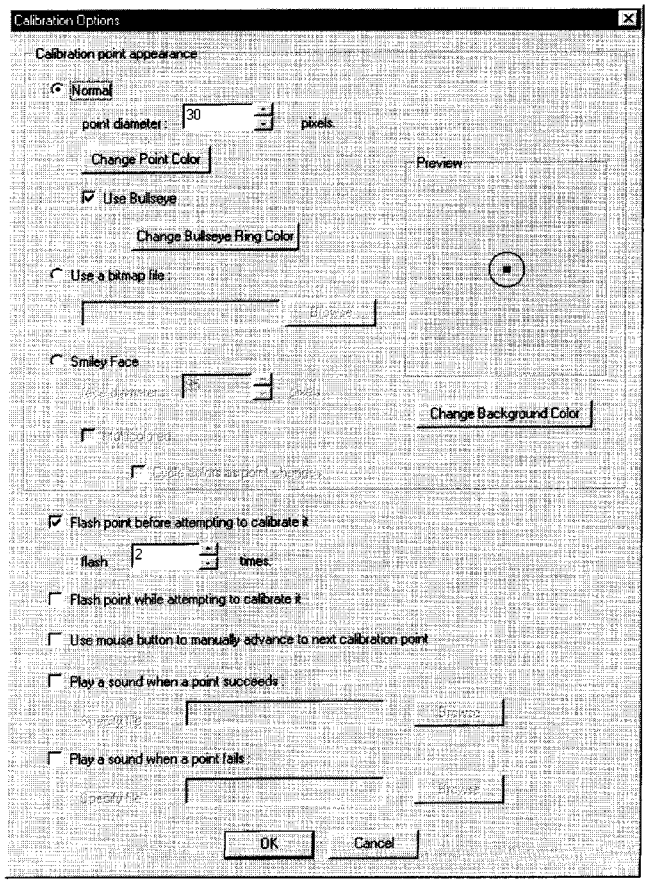

Figure 4.21: The Calibration Options Window.

Diagnostics

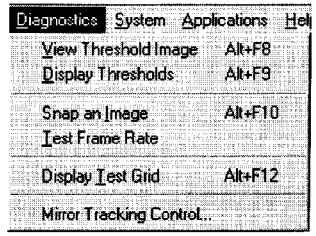

Figure 4.22: The Diagnostics menu

- *View Threshold Image*

Selecting this option will open a window in HQ which displays the user's image which was used to set the thresholds. The image appears on subsequent threshold settings. The image will show what ERICA thinks is the glint and pupil by bounding the two features with green boxes. A tight box on both of the features signifies a good threshold was set.

- *Display Thresholds*

Selecting this option will open a window in HQ that contains information about the current pupil and glint thresholds. The glint thresholds should always be above the pupil threshold. If it is not, then reset thresholds.

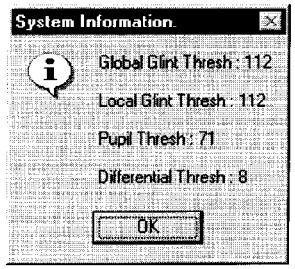

Figure 4.23: The System Thresholds

- *Snap an Image*

When this item is selected, the camera will take a picture of whatever it is currently viewing and display it on the screen.

- *Test Frame Rate*

This option will cause the ERICA system to test and display the current frame rate for image acquisition. If thresholds have been set, the system will attempt to identify features and will output the success rate.

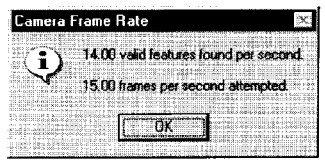

Figure 4.24: Test Frame Rate Window

- *Display Test Grid*

When this item is checked, HQ will display a test grid when mouse emulation is enabled. The test grid is a grid with points which enable the user to gauge current system accuracy. The points that are displayed are the same points that were presented during calibration. A ✓ indicates that *Display Test Gird* is currently enabled.

- *Mirror Tracking Control*

If you select this item, a new window will appear in HQ as shown in figure 4.32. By selecting any of the arrow keys, you can manually control the mirror on the ERICA system.

By selecting the *Details* option, you can also modify which serial port controls the mirror.

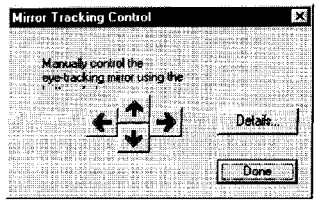

Figure 4.25: Mirror Tracking Control

System

Figure 4.26: The System Menu

- *Auto Enable System*

When this option is selected, HQ will automatically enable the system immediately following calibration. A ✓ indicates that *Auto Enable System* is enabled.

- *Auto Enable Mouse Emulation*

When this option is selected, HQ will automatically enable Mouse Emulation immediately following calibration. . A ✓ indicates that *Auto Enable Mouse Emulation* is enabled.

Applications

Figure 4.27: The Applications pull down menu

- *GazeTracker*

To start GazeTracker, move the cursor over this selection, and click *Start* from the sub-menu. You can also press *F9* to start GazeTracker.

- *Keyboard*

To start the Visual Keyboard, move the cursor over this selection, and click *Start* from the sub-menu.

- *AutoStart...*

Upon selecting this item, a new window will appear in HQ as shown in figure 4.31. If no applications are selected, the window will be mostly blank except for a checkbox at the top: *Automatically Load Applications upon completing calibration.* Select that box if you would like to specify applications you would like opened when HQ has finished calibrating.

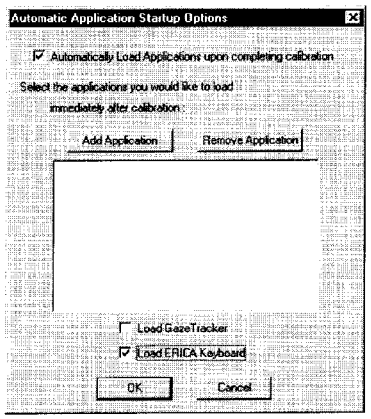

Figure 4.28: The AutoStart sub-window

*Add Application* – HQ has the ability to automatically open multiple applications when calibration has been completed. To do this, select the button *Add Application* from the AutoStart menu. A file dialog box will appear. You may then choose what program you would like executed when HQ has completed calibration. When you have highlighted the desired application, click the *Open* button. You will return to the AutoStart menu. Click the *Ok* button in this window to finalize your AutoStart selections.

When adding new applications to the Automatic Application Startup Menu, they will be placed at bottom of the list. In order to position a specific application in the list, first highlight the application in the list that you would like to place the new selection after, then add the new application to the list.

☞ Multiple instances of the same application may appear on the application list.

*Remove Application* - In order to remove an application from the AutoStart application list, first you must highlight it in the window by clicking on the selection. Then select the *Remove Application* button.

At the bottom of the window, two shortcuts have been provided for GazeTracker and the Visual Keyboard. Select these boxes if you would like the application(s) to load following calibration in HQ.
Help
Figure 4.29: Help Pull-Down Menu
- *About ERICA HQ*
    This option will display program information, version number and copyright..

Operations

☞ Operation Tip: It may be easier to perform these functions with the help of a partner. While you sit in position, your partner should make the necessary adjustments to the camera and mirrors as well as operate the mouse.

☞ The system requires that thresholds be set prior to calibration.

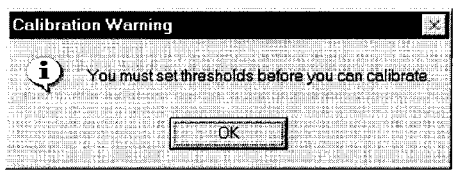

Figure 4.4: Warning Dialog to set thresholds before Calibration.

- *Set Threshold Icon:* Set/Not Set

The threshold setting function searches through the user's eye image and determines the brightness of the pupil and glint. These intensity values become the bright eye and glint threshold.

Click on the icon to set thresholds. During threshold setting, you will first be asked to first focus your eye on the camera LED, then to focus your eye on the large red dot that appears at the bottom of the screen. After setting the thresholds, this window will automatically close and return you to the HQ General Tab.

- *Calibrate Icon:* No calibration data/Have data

☞ Do not rush this step. Carefully focus your gaze on each point.

Calibration is the setup of ERICA to function with the specific data measurements of a particular user's eye. Regression algorithms are invoked to determine a "best fit" relationship between the known lookpoints and the calculated vectors. Once this relationship has been established, the information can be stored in a file for retrieval in future ERICA HQ sessions.

Click on the icon to calibrate. You will be asked to gaze at a number (18-36) of points which appear successively on the screen. Focus on each point while it is being displayed. The analysis data from the calibration can be viewed in the Calibration Tab.

System Control

- *Mouse Emulation Icon:* On/Off

To enable Mouse Emulation, click on the icon. This will also automatically enable the system. When Mouse Emulation is turned on, ERICA will move the mouse cursor to the gaze location. This is not used in the GazeTracker application, but it will allow you to become acquainted with an eye-controlled mouse and check for a successful calibration.

- *System Icon:* Enabled/Disabled

☞ System must be enabled for applications to obtain data from ERICA HQ.

☞ Thresholds must be set prior to enabling the system.

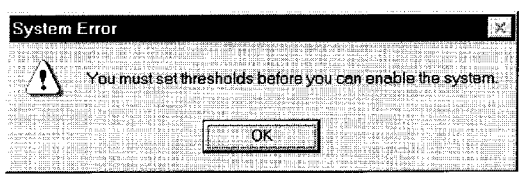

Figure 4.5: Warning Dialog to Set Thresholds.

To enable or disable the system, click the eye icon.

- *Minimize Icon:*

Click this icon to minimize the HQ window.

☞ When you have Set Thresholds, Calibrated and Enabled the system, ERICA HQ is ready for use with GazeTracker and/or other applications.

☞ Mouse emulation can be distracting and should not be on when running GazeTracker.

Chapter 4　　　　　　　　　　　　　　　　　　　　　　　　　　　ERICA HQ Menu Structure

System Control

- *Score:*

The score is a rating of the success and accuracy of the current calibration. Scores range from zero to 100, with 100 being the maximum score. A score of 95 or lower will be highlighted in red. Such scores are recommend to be recalibrated.

- *Points Failed:*

This number represents the number of points that failed in calibration. If you click the recalibrate icon, you can recalibrate just these points.

- *Recalibrate:*

Recalibrate any failed points.

Chapter 4 ERICA HQ Menu Structure

*Pull-Down Menus*

File

Figure 4.6: File Pull-Down Menu

- *New User*

This option allows you to restart the opening dialog sequence in order to calibrate and set up the ERICA system for a new user.

- *Save User*

This option will save the current calibration under your specified user ID.

- *Exit*

Selecting this option will close ERICA HQ.

View

Figure 4.7: View Pull-Down Menu

- *Status Bar*

The Status Bar is the gray bar the runs along the bottom of the HQ window. Most of the time, it will display the word *Ready* in the lower left-hand corner. It will also display helpful messages when certain options have been selected from the Pull-Down Menus. A ✓ indicates that the status bar is enabled.

A User's Guide to ERICA 4.6

Chapter 4                                                                                                ERICA HQ Menu Structure

Control

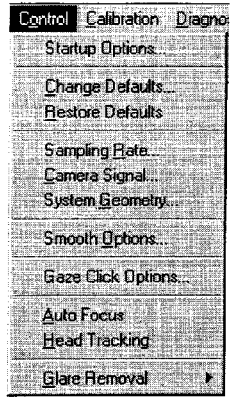

Figure 4.8: Control Pull-Down Menu

The Control menu options access many of the same functions that may have been initialized in the Opening Dialog Sequence.

- *Startup Options...*

When Startup Options is selected, a new window will open in HQ entitled HQ Startup Options. This window contains setup and calibration options that are available when HQ is opened. By default, the options *Set Thresholds, Then Calibrate* and *Large Calibration*, will all be checked. This means that when ERICA HQ is executed, it will automatically prompt the user to *Set Thresholds* and then perform a *Large Calibration*.

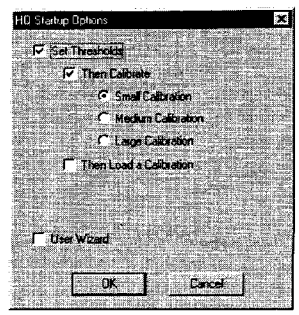

Figure 4.9: The Startup Options

A User's Guide to ERICA 4.7

*Set Thresholds* - When this item is checked, ERICA HQ will prompt the user to set the system thresholds at the start of HQ execution. If this item is checked, the user has the choice of either leaving both Calibration options blank and skipping that procedure, or choosing either to *Calibrate* or to *Load a Calibration*.

> *Calibrate* - If this item is checked, ERICA HQ will prompt the user to set the system thresholds and then calibrate the system. You may choose between either a *Small Calibration* or a *Large Calibration*.

☞ The difference between a *Small Calibration* and a *Large Calibration* is the number of points that are presented to the user in order to calibrate the system. A *Small Calibration* takes less time, but is also less accurate than the *Large Calibration*. A *Large Calibration* is always recommended for greater system accuracy.

> *Load Calibration* - This option tells HQ to load a previously saved calibration when HQ is opened. When this item is checked, a box will appear for the user to enter the desired User ID.

☞ A valid User ID must be entered in the box for this option to perform correctly.

*User Wizard* - If this selection is checked, HQ will guide the user through a step-by-step calibration process at the beginning of HQ. This process is detailed in Chapter 3 of this instruction manual.

☞ The ERICA system will not operate if thresholds have been set, but calibration
   has not been performed.

- *Change Defaults...*

You may change the system defaults by selecting this item. This option is password protected.

- *Restore Defaults*

Selecting this option will restore all settings to their default values.

- *Sampling Rate ...*

The Sampling Rate is the frequency at which ERICA attempts to estimate the user's gaze point. We suggest the maximum setting of 15 frames per second. For more details, see page 4.4.

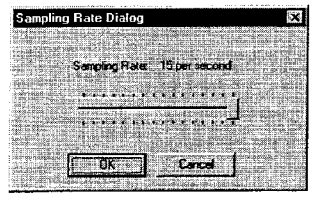

Figure 4.10: Sampling Rate Dialog.

- *Camera Signal ...*

☞ Making an adjustment to the offset or gain may cause system inaccuracy in the detection of glares and require readjustment of the Glare Threshold value. Therefore it is strongly recommended that you not change these values.

Offset (0-255)
    This operation allows you to adjust the brightness of the image by adjusting the DC offset of the incoming camera signal. The default setting is 128.

Gain (0-255)
    This operation allows you to adjust the black and white contrast of the image. The default setting is 30.

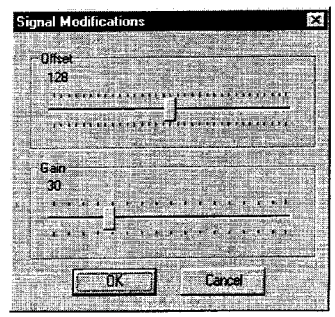

Figure 4.11: Signal Modifications Dialog.

- *System Geometry ...*

LED Separation Fraction
  : The LED Separation Fraction informs ERICA HQ of the position of the LED in relation to the monitor. The value entered is the distance from the LED (camera lens center) to the bottom of the display screen divided by the screen height. The default setting is 0.35. For an alternative method of adjusting the Separation Fraction, see page 4.8.

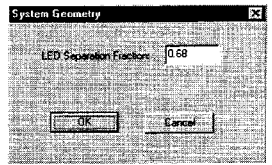

Figure 4.12: System Geometry Dialog.

- *Smooth Options ...*

As Chapter 3 explains, smoothing is a process in which the current screen point is averaged with several previously estimated gaze points. This reduces cursor jitter due to digitization artifacts and ensures that the screen pointer stays largely fixed when the user is looking at a single point on the screen.

Smooth filter point count (1-30)
  : This is a count of the number of points that are included in each smoothing average. We recommend a count of at least 1.

Throw out distance
  : The throw out distance is the maximum distance (in screen pixels) from the current screen point that the previous gaze points must fall within. Points outside this distance will be excluded in the smoothing average. An optimal throw out distance is 40 pixels.

Minimum movement distance
> This is the minimum distance (in screen pixels) between the current point and the smoothing averaged point. Smoothing will not be executed for distances less than this distance. We recommend a value of 5 pixels.

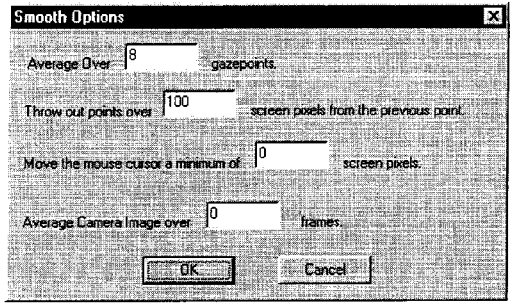

Figure 4.13: Smooth Options Window.

Camera Frame Average
> This averages glint and pupil relative distance over several frames to decrease cursor jittering. The recommended optimal value is 5.

- *Gaze Click Options...*

When you select this option a new window will open in HQ entitled "Gaze Click Options". Within this window will be one option named *Enable Gaze Clicking*. When the item is checked, the window will present you with a number of features shown in the figure below:

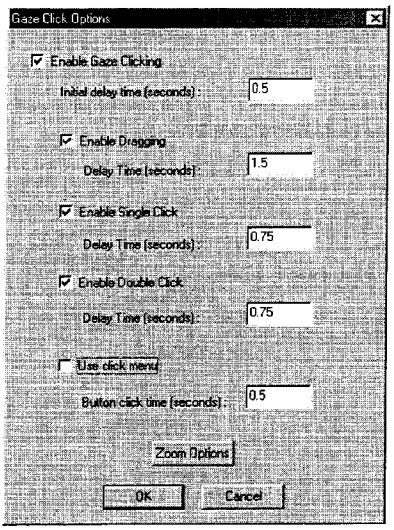

Figure 4.14: The Gaze Click Options window

*Initial Delay Time* - The *Initial Delay Time* is the duration of time before the red box starts collapsing when the user's gaze focus is stationary. The default value is .5 seconds.

*Enable Dragging* - This option enables you to click-and-drag items across the Windows environment. A ✓ indicates that *Dragging* is enabled. In the Windows environment, the ERICA system will display a two-stage collapsing box. The first stage takes place between the start of the collapse and halfway to a fully collapsed box. At this point, the collapsing box will become a circle and continue to collapse. When the circle is blue, you may drag the selected object by shifting your gaze. When you focus your gaze on the point where you would like the object dragged drag to, the box will collapse again. At the halfway point of this collapsing box, the item will automatically be released.

> *Dragging Delay Time* - This is the time it takes after the *Initial Delay Time* for the box to reach the blue halfway point. If the *Initial Delay Time* is set at .5 seconds, and the *Dragging Delay Time* is set for .5 seconds, than it will take 1 second after the cursor is stationary before you can drag an item.

*Enable Single Click* - This option enables the user to register single clicks through the ERICA system. A ✓ indicates that *Single Click* is enabled.

> *Single Click Delay Time* - This is the time it takes after the last option for a single click to occur. If *Dragging* is enabled, then the total time to click is equal to the *Initial Delay Time* plus the *Dragging Time* plus the *Click Time*. If *Dragging* is not enabled, then it is merely the time after the *Initial Delay Time*.

*Enable Double Click* - This option enables the user to register a double click through the ERICA system. A ✓ indicates that *Double Click* is enabled.

> *Double Click Delay Time* - This option operates identically to the above delay time options.

*Use Click Menu* - Instead of using the above clicking system, HQ also has a set of menu options that can be accessed whenever the user fixates his or her gaze in an area for a pre-determined amount of time. The menu is shown below in figure 4.15.

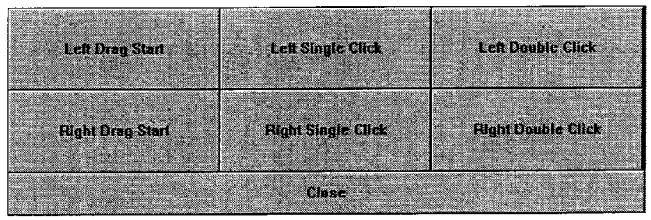

Figure 4.15: The Click Menu

*Zoom Options Button* – When the *Zoom Options* button is clicked, a new window will open as appears in figure 4.16. This window will enable you to customize the zoom options that HQ provides. The lower half of this window contains a preview space where the user may view a zoom example while customizing the features.

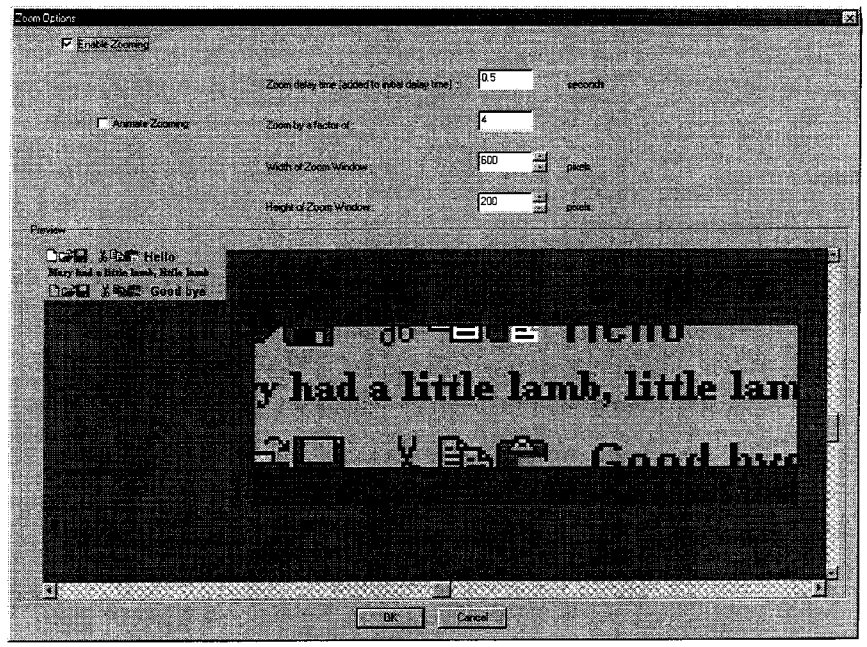

Figure 4.16: Zoom Options

*Enable Zooming* - When this item is checked, zooming will be enabled. Zooming occurs whenever the user fixates on an area for a certain amount of time and the system is enabled. HQ will take the area around where the click originated from and zoom it in a provided window space. The user may then click on any area within the zoom window, enabling a much higher accuracy.

*Animate Zooming* - When this item is checked, the zoom window will grow out of the collapsing rectangle.

*Zoom Delay Time* - This is the amount of time in seconds that must elapse after the initial delay time before zooming takes place.

*Width of Zoom Window* - This option enables the user to specify the zoom window width.

*Height of Zoom Window* - This options enables the user to specify the zoom window height.

- *Auto Focus*

Using this selection, you may either enable or disable the automatic focusing of the camera by ERICA. This function should be turned off if you are manually focusing the camera using the focusing knob on the ERICA system. A ✓ indicates that *Auto Focus* is enabled. In addition, to turn *Auto Focusing* on, a switch in the back right of the box must be flipped down. To use the knobs, the switch must be flipped up.

- *Head Tracking*

The ERICA system is capable of automatically tracking the user's head to keep the user's eye within the camera range. Toggling this feature enables you to have a small amount of lateral movement without disrupting the ERICA system. A ✓ indicates that Head Tracking is enabled.

- *Glare Removal*

ERICA HQ is designed to detect and remove glares that are a result of glasses worn by the user. In general, contact lenses do not produce such glare and should not have an effect on determining glint or bright eye position. Glares cause false glint and pupil detection and defeat the gaze find algorithm. If glasses are not being worn, this option can be disabled.

Glasses have a radius of curvature much larger than the white part of the eye (the sclera). This results in a glare that is larger than the glint and frequently of greater intensity. A glare removal algorithm is designed to blank these high intensity, large areas. When glares which fall on the glint and/or pupil are removed, however, the respective eye feature is also removed. So it is imperative that the glares not rest on top of the pupil or glint. High IR sources external to the system such as a window or incandescent lights can cause glares that are difficult for the system to accommodate. Thus high IR sources should be eliminated if possible.

Automatic Glare Detection

By default, automatic glare detection is enabled. A ✓ indicates that automatic glare detection is enabled. *Enabled* and *Disabled* options appear gray, but a ✓ indicates glare detection by the system. A ✓ by *Enabled* indicates that every detected glare will be removed.

Figure 4.17: Automatic Glare Detection Enabled.

☞ After Enabling *Automatic Glare Detection*, you should *Set Thresholds* again to ensure system accuracy after toggling *Auto Glare detection*.

To disable *Automatic Glare Detection*, click on the menu command. Then the *Enabled* and *Disabled* functions can be selected manually.

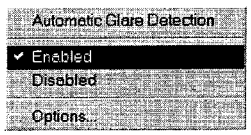

Figure 4.18: Manual Selection of Glare Detection.

☞ After Enabling *Glare Detection*, you should *Set Thresholds* again to ensure system accuracy after toggling *Glare detection*.

Options

Pixel Length (pixels): Minimum number of pixels of a bright spot on the image for the system to consider the spot a glare. We suggest a value of 2 pixels.

Glare Threshold: Minimum intensity for a pixel to be considered part of a glare. We recommend a setting of 200.

Adjustment Factor: The amount by which the glare threshold is adjusted once a glare is detected. We suggest that this value remain at 80. This allows the halo around a glare to be removed as well.

Search Scheme: These options are intended for advanced users. You may choose whether you would like the ERICA system to search for glare *Vertically, Horizontally* or both ways. You also have the option of selecting how many lines at a time these searches are done. Choosing a search scheme of both and a search of 1 line vertically and 1 line horizontally will result in maximum glare elimination, but performance will suffer. Thus, we recommend a search scheme of horizontal and 2 vertically, 2 horizontal for increased performance.

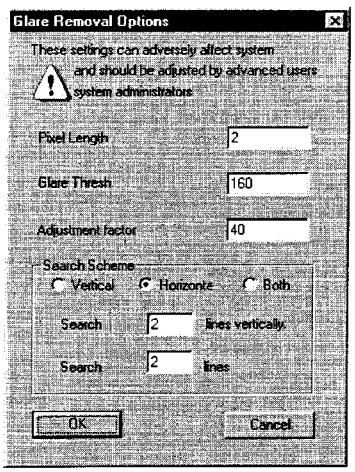

Figure 4.19: Glare Removal Options Dialog.

Chapter 4                                                    ERICA HQ Menu Structure Table 4.1: ERICA HQ Control Functions.

| Control Function | Default Value | Range | Reasons for changing default value |
|---|---|---|---|
| Sampling Rate | 15 frames/sec | 0-15 frames/sec | Applications requiring system efficiency |
| *Camera Signal Options* | | | |
| Offset | 128 | 0-255 | Adjusts brightness of image |
| Gain | 30 | 0-255 | Adjusts contrast of image |
| *System Geometry* | | | |
| LED Separation Fraction | 0.35 | 0-1 | None |
| *Smooth Options* | | | |
| Smooth filter point count | 1 points | 1-30 points | Adjusts number of points used in cursor placement |
| Throw out distance | 40 pixels | 0-2000 pixels | May help eliminate "cursor jitter" |
| Minimum movement distance | 10 pixels | 0-500 pixels | May help eliminate "cursor jitter" |
| *Glare Removal Options* | | | |
| Glare Length | 2 pixel | 0-640 pixels | None |
| Glare Threshold | 200 | 0-255 | Requires adjustment if changes are made to camera signal options |
| Adjustment Factor | 80 | 1-1000 | None |

Chapter 4                                                    ERICA HQ Menu Structure

Calibration

Figure 4.20: Calibration Pull-Down Menu.

- *Small*

When this selection is checked, HQ will perform a *small* calibration when the Calibrate button is clicked.

- *Medium*

*I*   When this selection is checked, HQ will perform a *medium* calibration when the Calibrate button is clicked.

- *Large*

When this selection is checked, HQ will perform a *large* calibration when the Calibrate button is clicked.

☞ The difference between a *Small Calibration* and a *Large Calibration* is the number of points that are presented to the user in order to calibrate the system. A *Small Calibration* takes less time, but is also less accurate than the *Large Calibration*. A *Large Calibration* is always recommended for system accuracy.

- *Options...*

The *Options* menu will enable the user to set the different calibration options that are available. Calibration can be a long and uninteresting process, especially for children. Thus ERICA provides alternate calibration markers from the tradition target. The user may change colors, use a smiley face, or use his or her own bitmap file for calibration. Other options are included so that the user may find what works best for the himself or herself. These options can be seen in figure 4.21.

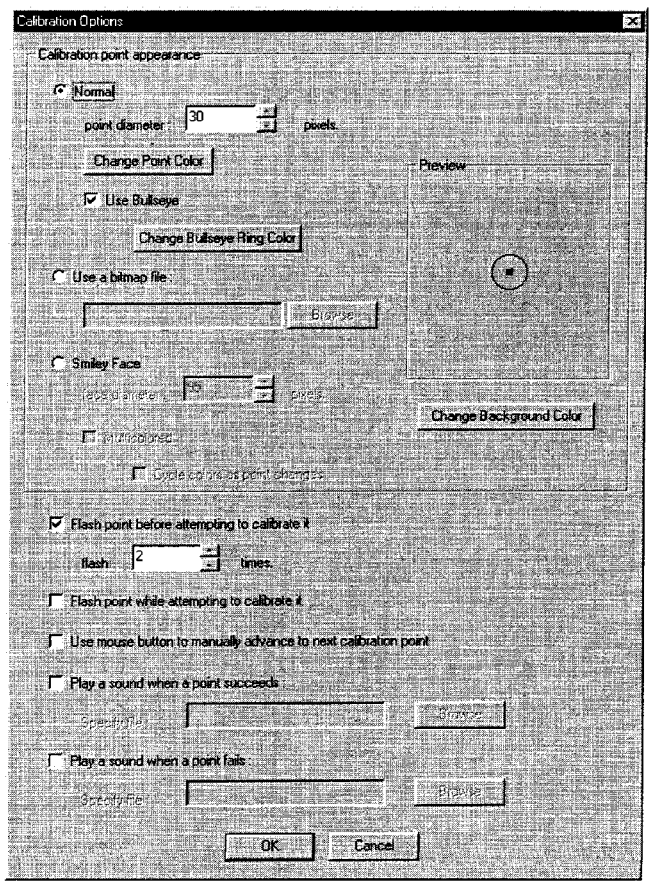

Figure 4.21: The Calibration Options Window.

Chapter 4                                           ERICA HQ Menu Structure

Diagnostics

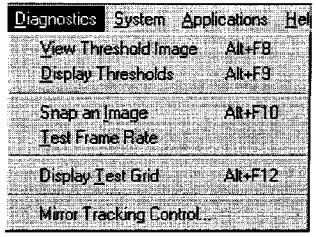

Figure 4.22: The Diagnostics menu

- *View Threshold Image*

Selecting this option will open a window in HQ which displays the user's image which was used to set the thresholds. The image appears on subsequent threshold settings. The image will show what ERICA thinks is the glint and pupil by bounding the two features with green boxes. A tight box on both of the features signifies a good threshold was set.

- *Display Thresholds*

Selecting this option will open a window in HQ that contains information about the current pupil and glint thresholds. The glint thresholds should always be above the pupil threshold. If it is not, then reset thresholds.

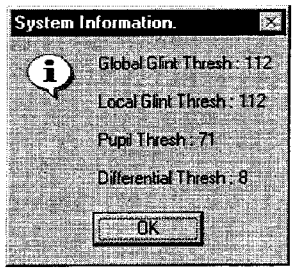

Figure 4.23: The System Thresholds

A User's Guide to ERICA 4.21

- *Snap an Image*

When this item is selected, the camera will take a picture of whatever it is currently viewing and display it on the screen.

- *Test Frame Rate*

This option will cause the ERICA system to test and display the current frame rate for image acquisition. If thresholds have been set, the system will attempt to identify features and will output the success rate.

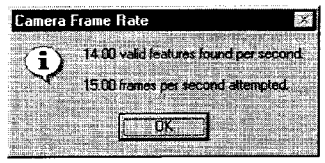

Figure 4.24: Test Frame Rate Window

- *Display Test Grid*

When this item is checked, HQ will display a test grid when mouse emulation is enabled. The test grid is a grid with points which enable the user to gauge current system accuracy. The points that are displayed are the same points that were presented during calibration. A ✓ indicates that *Display Test Gird* is currently enabled.

- *Mirror Tracking Control*

If you select this item, a new window will appear in HQ as shown in figure 4.32. By selecting any of the arrow keys, you can manually control the mirror on the ERICA system.

By selecting the *Details* option, you can also modify which serial port controls the mirror.

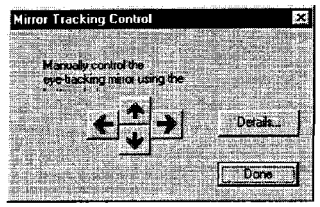

Figure 4.25: Mirror Tracking Control

Chapter 4            ERICA HQ Menu Structure

System

Figure 4.26: The System Menu

- *Auto Enable System*

When this option is selected, HQ will automatically enable the system immediately following calibration. A ✓ indicates that *Auto Enable System* is enabled.

- *Auto Enable Mouse Emulation*

When this option is selected, HQ will automatically enable Mouse Emulation immediately following calibration. . A ✓ indicates that *Auto Enable Mouse Emulation* is enabled.

Applications

Figure 4.27: The Applications pull down menu

- *GazeTracker*

To start GazeTracker, move the cursor over this selection, and click *Start* from the sub-menu. You can also press *F9* to start GazeTracker.

- *Keyboard*

To start the Visual Keyboard, move the cursor over this selection, and click *Start* from the sub-menu.

- *AutoStart...*

A User's Guide to ERICA

What is claimed is:

1. A system for eve-gaze direction detection said system comprising an infrared light source means to protect said light source upon the eye of a user of a system employing the eye-gaze direction system, a video camera means adapted to view the position of the glint-pupil relationships of the users eye, a computing means adapted to assist in computing the eye position of the user so as to calibrate the system to the users eye movements whereby the system may be used to control the interaction between a computer/monitor system and the user, wherein said video camera means has a frame grabber card associated therewith.

2. A system as in claim 1 wherein the card acquires the image and digitizes it into a sequence of pixels and maps the pixels into the system memory.

3. A system as in claim 2 wherein the system checks to see, once the image is acquired, if any glares are present in a predetermined sequence.

4. A system for eye-gaze direction detection, said system comprising an infrared light source means to project said light source upon the eye of a user of a system employ employing the eye-gaze direction system, a video camera means adapted to view the position of the glint-pupil relationships of a users eye, a computing means adapted to assist in computing the eye position of the user so as to calibrate the system to the users eye movements whereby the system may be used to control the interaction between a computer/monitor system and the user, and including mirrors positioned to bounce the infra red light source onto the users eye and to bounce the reflection back to the video means.

5. The method of controlling a computer system which has a graphic display by eye movement alone, said method comprising fixating one's gaze upon a specific area of said display to produce a window which is a magnification of that specific area and which contains specific information, again fixating one's gaze upon the window to produce a menu of specific actions and fixating one's gaze upon that specific action that one desires the computer to initiate whereby one had interacted with the computer with only eye movement.

6. The method of claim 5 including the steps of fixating ones gaze initially to an area of the monitor to turn the computer system on.

7. The method of claim 6 which includes the step of the user first setting thresholds and to calibrate the system by making initial eye movements to allow the system to calibrate the equations used to map angles and radii between the pupil and glint centers of the users eye to radii and angles on the screen.

8. The method of claim 5 including the step of physically activating a computer key to allow the user to drag items on the screen across the screen by fixating on that item and then dragging it while the computer key is depressed.

9. The method of claim 5 including the step of releasing said key to allow said item to stay where the users gaze has left it.

10. A method of calibrating an eye-gaze computer control system which is directed solely by user eye gaze fixation upon the computer display as an interactive user control means, said method comprising directing an infra-red bean upon the users eye to detect the glint-pupil relationships, viewing the glint-pupil relationships and establishing a grid therefrom on which to measure all future user eye movements in relationship to the display, and establishing, through angles and radii, lines of calibration points from which to calibrate all future user eye movements.

11. A method as in claim 10 wherein a regression equation is used during system operation to determine where the user is looking.

12. A method as in claim 10 including the initial step of causing the user to initiate said eye only control.

* * * * *